(12) United States Patent
Ambroso et al.

(10) Patent No.: US 11,613,778 B2
(45) Date of Patent: Mar. 28, 2023

(54) LONG LIFETIME ALPHA-HEMOLYSIN NANOPORES

(71) Applicant: Roche Sequencing Solutions, Inc., Pleasanton, CA (US)

(72) Inventors: Mark Ambroso, San Diego, CA (US); Timothy Craig, Campbell, CA (US); Matthew DiPietro, Gilroy, CA (US); Corissa Harris, Santa Clara, CA (US); Marshall Porter, Petaluma, CA (US)

(73) Assignee: Roche Sequencing Solutions, Inc., Pleasanton, CA (US)

( * ) Notice: Subject to any disclaimer, the term of this patent is extended or adjusted under 35 U.S.C. 154(b) by 0 days.

(21) Appl. No.: 17/157,576

(22) Filed: Jan. 25, 2021

(65) Prior Publication Data

US 2021/0230683 A1    Jul. 29, 2021

Related U.S. Application Data

(63) Continuation of application No. 16/519,251, filed on Jul. 23, 2019, now Pat. No. 10,934,582, which is a continuation of application No. 15/638,273, filed on Jun. 29, 2017, now abandoned.

(60) Provisional application No. 62/357,230, filed on Jun. 30, 2016.

(51) Int. Cl.
  *C07K 14/00* (2006.01)
  *C12Q 1/6869* (2018.01)
  *C07K 14/31* (2006.01)
  *A61K 38/02* (2006.01)
  *C12N 15/01* (2006.01)

(52) U.S. Cl.
  CPC ............ *C12Q 1/6869* (2013.01); *A61K 38/02* (2013.01); *C07K 14/31* (2013.01); *C12N 15/01* (2013.01); *C07K 14/00* (2013.01)

(58) Field of Classification Search
  CPC .................................................. C12Q 1/6869
  See application file for complete search history.

(56) References Cited

U.S. PATENT DOCUMENTS

| 10,968,480 B2 | 4/2021 | Craig |
| 2017/0306397 A1* | 10/2017 | Craig ............... G01N 27/44791 |
| 2021/0269870 A1 | 9/2021 | Craig |

FOREIGN PATENT DOCUMENTS

| CN | 103267785 A | 8/2013 |

* cited by examiner

*Primary Examiner* — Albert M Navarro
(74) *Attorney, Agent, or Firm* — FisherBroyles, LLP; Jason M. Pass

(57) ABSTRACT

Described herein are variants of alpha-hemolysin having at least one amino acid substitution at H35G, E111N, M113A, and/or K147N in the mature, wild-type alpha-hemolysin amino acid sequence. In certain examples, the variant may have a substitution at E111S, M113S, T145S, K147S, or L135I in the mature alpha-hemolysin amino acid sequence. The α-hemolysin variants may also include a substitution at H144A and/or a series of glycine residues spanning residues 127 to 131 of the mature, wild-type alpha hemolysin. Also provided are nanopore assemblies including the alpha-hemolysin variants, the assembly having an increased nanopore lifetime. Further, provided are variants that, in addition to providing increased lifetime, provide a decreased time-to-thread. Hence, the variants provided herein both increase nanopore lifetime and improve efficiency and accuracy of DNA sequencing reactions using nanopores comprising the variants.

18 Claims, 4 Drawing Sheets

Specification includes a Sequence Listing.

LONG LIFETIME ALPHA-HEMOLYSIN NANOPORES

RELATED APPLICATIONS

This application is a continuation application of U.S. application Ser. No. 16/519,251, filed Jul. 23, 2019, which is a continuation of U.S. application Ser. No. 15/638,273, filed Jun. 29, 2017, which application claims the benefit of U.S. Provisional Application Ser. No. 62/357,230, filed on Jun. 30, 2016, the contents of which are hereby incorporated in their entirety.

SEQUENCE LISTING INCORPORATION BY REFERENCE

This application hereby incorporates-by-reference a sequence listing submitted herewith in a computer-readable format, having a file name of 04338_539US3_seqlist, created on Jan. 25, 2021, which is 55 KB in size.

TECHNICAL FIELD

Disclosed are methods and compositions relating to *Staphylococcus aureaus* alpha-hemolysin variants that, when assembled into a multi-subunit nanopore, increase the sequencing lifetime of the nanopore during a nucleic acid sequencing reaction. Also disclosed are variants that, when assembled into a multi-subunit nanopore, improve sequencing efficiency and accuracy.

BACKGROUND

Hemolysins are members of a family of protein toxins that are produced by a wide variety of organisms. Some hemolysins, for example alpha hemolysins, can disrupt the integrity of a cell membrane (e.g., a host cell membrane) by forming a pore or channel in the membrane. Pores or channels that are formed in a membrane by pore forming proteins can be used to transport certain polymers (e.g., polypeptides or polynucleotides) from one side of a membrane to the other.

Alpha-hemolysin (α-HL, a-HL or alpha-HL) is a self-assembling hemolysin toxin that forms a channel in the membrane of a host cell. More particularly, seven alpha-hemolysin monomers assemble into a heptameric, beta-barrel pore in biological membranes. Alpha-hemolysin has many advantageous properties including high stability and self-assembly into a nanopore that is wide enough to accommodate single stranded DNA but not double stranded DNA (Kasianowicz et al., 1996). Based on these properties and other properties, alpha-hemolysin has become a principal component for the nanopore sequencing community.

Previous work on DNA detection in the a-HL pore has focused on analyzing the ionic current signature as DNA translocates through the pore (Kasianowicz et al., 1996, Akeson et al., 1999, Meller et al., 2001), a very difficult task given the translocation rate (~1 nt/µs at 100 mV) and the inherent noise in the ionic current signal. Higher specificity has been achieved in nanopore-based sensors by incorporation of probe molecules permanently tethered to the interior of the pore (Howorka et al., 2001a and Howorka et al., 2001b; Movileanu et al., 2000).

While the use of nanopores has revolutionized DNA sequencing, nanopores using wild-type alpha-hemolysins are only able to generate sequence data for a short amount of time. Hence, the lifetime of the alpha-hemolysin nanopore during the sequencing reaction often serves as the rate-limiting feature of the sequencing reaction. Further, use of wild-type alpha hemolysin often results in a significant number of deletion errors, i.e., bases that are not measured. Therefore, alpha-hemolysin nanopores with improved properties, including increased sequencing lifetimes, are desired.

BRIEF SUMMARY OF THE INVENTION

Provided herein are mutant staphylococcal alpha hemolysin (αHL) polypeptides that, when incorporated into a nanopore, improve the lifetime of the nanopore during a DNA sequencing reaction. For example, a nanopore including one or more of the variants described herein lasts longer—and hence provides more sequencing data—than a nanopore that consists of wild-type alpha hemolysin.

In certain example aspects, the α-hemolysin (α-HL) variants comprise a substitution at a position corresponding to any one of E111N, M113A, K147N, or a combination thereof of SEQ ID NO: 14 (the mature, wild-type alpha hemolysin sequence). The α-hemolysin variant may also include a substitution at H35G or K135G of SEQ ID NO: 14. The α-hemolysin variant may also, in certain aspects, include one or more one or more glycine residues at residues 126-131 of SEQ ID NO: 14, such as a series of glycine residues that span the entire length of residues 126 through 131 of SEQ ID NO: 14. For example, the variant may also include a poly-G substitution corresponding to amino acids 127-129 of the amino acid sequence set forth as SEQ ID NO: 14, resulting in a span of glycine residues from 126 through 131 of SEQ ID NO: 14.

In certain example aspects, the α-hemolysin variant includes an amino acid sequence having at least one of the substitutions described herein, while the sequence of the α-hemolysin variant has at least 80%, 90%, 95%, 98%, or more sequence identity to the amino acid sequence set forth as SEQ ID NO: 14. In certain example aspects, the α-hemolysin variant includes an amino acid sequence having at least 80%, 90%, 95%, 98%, or more sequence identity to the amino acid sequence set forth as SEQ ID NOS: 17, 18, 19, 20, or 22.

In certain example aspects, the alpha-hemolysin variant described herein is bound to a DNA polymerase, such as via a covalent bond. For example, the alpha-hemolysin variant is bound to the DNA polymerase via a SpyTag/SpyCatcher linkage. In certain example aspects, the alpha-hemolysin variant is bound to the DNA polymerase via an isopeptide bond.

In certain example aspects, provided is a heptameric nanopore assembly. The assembly, for example, includes at least one or more of the alpha-hemolysin variants described herein. For example, the heptameric nanopore assembly may include one or more alpha-hemolysin proteins having a substitution at E111N, M113A, K147N, or combinations thereof of SEQ ID NO: 14, such as described herein. In certain example aspects, the heptameric nanopore assembly may include one or more alpha-hemolysin proteins having a substitution at E111S, M113S, T145S, K147S or L135I or combinations thereof of SEQ ID NO: 14, such as described herein. In certain example aspects, each of the seven alpha-hemolysin monomers of the heptameric nanopore are alpha-hemolysin variants as described herein. The variant can be the same variant or a combination of different variants described herein. In certain example aspects, the nanopore assembly includes one or more variants having at least 80%, 90%, 95%, 98%, or more sequence identity to the amino acid sequence set forth as SEQ ID NOS: 17, 18, 19, 20, or 22. By using and relying on the alpha-hemolysin variants to assemble the nanopore, in certain example aspects the lifetime of the resultant nanopore is increased by 5%, 10%, 20%, 30%, 40%, 50%, 60%, 70%, 80% or more when compared to a heptameric nanopore assembly consisting of native alpha-hemolysin.

In certain example aspects, also provided are nucleic acids encoding any of the alpha hemolysin variants described herein. For example, the nucleic acid sequence can be derived from *Staphylococcus aureus* (SEQ ID NO: 1). Also provided, in certain example aspects, are vectors that include an any such nucleic acids encoding any one of the hemolysin variants described herein. Also provided is a host cell that is transformed with the vector.

In certain example aspects, provided is a method of producing an alpha-hemolysin variant as descried herein. The method includes, for example, the steps of culturing a host cell including the vector in a suitable culture medium under suitable conditions to produce alpha-hemolysin variant. The variant is then obtained from the culture using methods known in the art.

In certain other example aspects, provided is a method of detecting a target molecule. The method includes, for example, providing a chip comprising a nanopore assembly as described herein in a membrane that is disposed adjacent or in proximity to a sensing electrode. The method then includes directing a nucleic acid molecule through the nanopore. The nucleic acid molecule is associated with a reporter molecule and includes an address region and a probe region. The reporter molecule is associated with the nucleic acid molecule at the probe region and is coupled to a target molecule. The method further involves sequencing the address region while said nucleic acid molecule is directed through said nanopore to determine a nucleic acid sequence of said address region. The target molecule is identified, with the aid of a computer processor, based upon a nucleic acid sequence of the determined address region determined.

These and other aspects, objects, features and advantages of the example embodiments will become apparent to those having ordinary skill in the art upon consideration of the following detailed description of illustrated example embodiments. It should be understood, however, that the detailed description and specific examples, while indicating preferred embodiments of the invention, are given by way of illustration only, since various changes and modifications within the scope and spirit of the invention will become apparent to one skilled in the art from this detailed description.

BRIEF DESCRIPTION OF THE DRAWINGS

FIG. 2 represents an analog to digital converter (ADC) value for our AC coupled system, which gives rise to an ADC value for open channel when the applied bias is positive (175 ADC units) and when the applied bias is negative (45 ADC units). When a tagged nucleotide is threaded into the pore, the ADC value during the application of positive bias decreases from the open channel level to 145 ADC units. Several examples of this are shown from 1020 to 1040s in the expanded lower panel of FIG. 4B. When the applied bias is negative, the tagged nucleotide exits the pore, which is why the negative open channel level is not significantly reduced. In order to calculate the threading rate, a distribution of the times required in each positive bias period for the ADC value to reach a threaded level is counted for cycles whose immediately prior cycle ended at a threaded ADC value. This histogram is then fit to a standard single exponential function, whose decay rate is the threading rate.

DETAILED DESCRIPTION

Figure 1A:
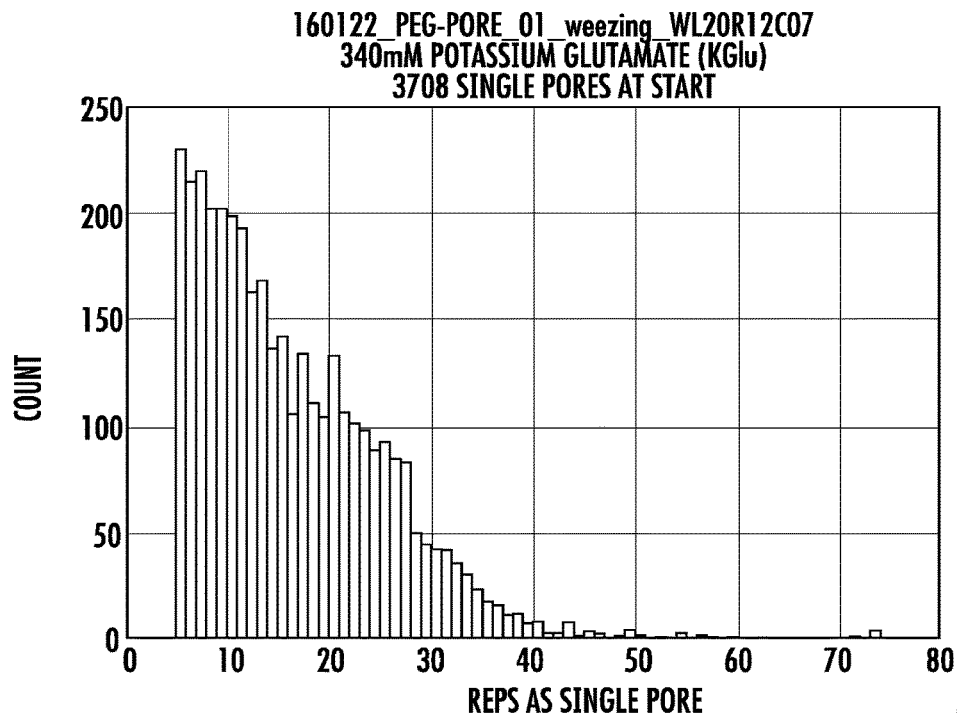
FIG. 1A is histogram showing lifetime assessment for a standard H144A nanopore. The y-axis is the number of pores which had a lifetime within the bin on the x-axis. The x-axis is the number of 100s intervals (reps) in which the current passing through the channel corresponded to that of a single Hemolysin nanopore. This experiment was run for 7200s, or 72 reps.
Figure 1B:
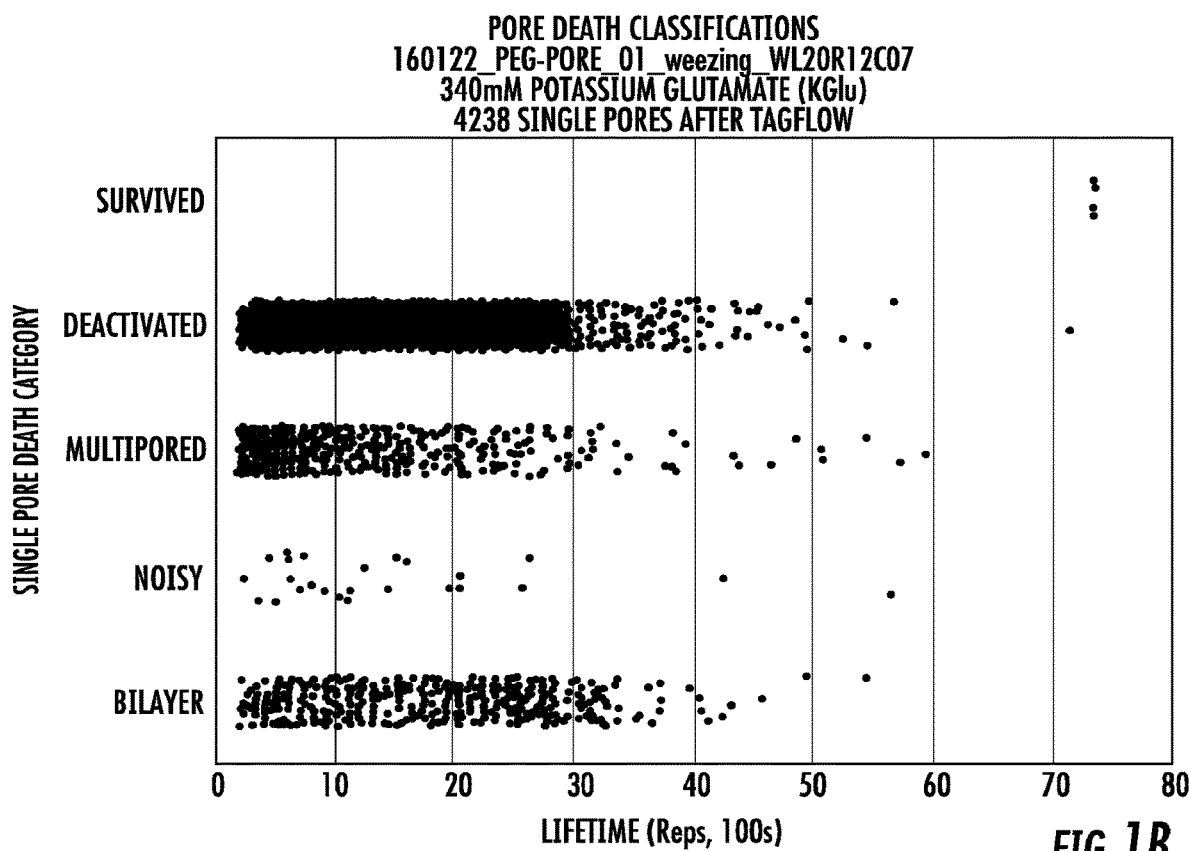
FIG. 1B is a graph showing an analysis of the failure mechanisms of the H144A nanopore for the same run as FIG. 1A. This experiment was run for 7200s, or 72 reps. represents an analysis of the failure mechanisms of the nanopore for the same run as FIG. 1A. As shown, individual pores are displayed as dots in a number of categories. The first category is for those pores which survived until the end of the experiment; their mode of failure was that the instrument was shut off. The second category is for cells that were turned off by the Genia FPGA because the current increased very quickly to a level >10× of the current of a single nanopore, which is a general indicator that the lipid bilayer was disrupted. The third category is for when the open channel current increases from that of a single pore to that of a multiple of a single pore, but lower than 10× the current. This typically indicates that 2, 3, 4, 5, 6, 7, 8, or 9 nanopores inserted into the bilayer that originally only harbored one. The noisy bin contains pores where some unknown mode of failure occurred, which typically results in an unstable level of current is being measured; these may be due to electrode failure. The last category is bilayer, and corresponds to the situation where current is no longer measured passing through a nanopore, but rather the characteristically low conductance of a lipid bilayer is seen.

The embodiments described herein can be understood more readily by reference to the following detailed description, examples, and claims, and their previous and following description. Before the present system, devices, compositions and/or methods are disclosed and described, it is to be understood that the embodiments described herein are not limited to the specific systems, devices, and/or compositions methods disclosed unless otherwise specified, as such can, of course, vary. It is also to be understood that the terminology used herein is for the purpose of describing particular aspects only and is not intended to be limiting.

Further, the following description is provided as an enabling teaching of the various embodiments in their best, currently known aspect. Those skilled in the relevant art will recognize that many changes can be made to the aspects described, while still obtaining the beneficial results of this disclosure. It will also be apparent that some of the desired benefits of the present invention can be obtained by selecting some of the features of the various embodiments without utilizing other features. Accordingly, those who work in the art will recognize that many modifications and adaptations to the various embodiments described herein are possible and can even be desirable in certain circumstances and are a part of the present disclosure. Thus, the following description is provided as illustrative of the principles of the embodiments described herein and not in limitation thereof.

The invention will now be described in detail by way of reference only using the following definitions and examples. All patents and publications, including all sequences disclosed within such patents and publications, referred to herein are expressly incorporated by reference.

Unless defined otherwise herein, all technical and scientific terms used herein have the same meaning as commonly understood by one of ordinary skill in the art to which this invention belongs. Singleton, et al., DICTIONARY OF MICROBIOLOGY AND MOLECULAR BIOLOGY, 2D ED., John Wiley and Sons, New York (1994), and Hale & Marham, THE HARPER COLLINS DICTIONARY OF BIOLOGY, Harper Perennial, N.Y. (1991) provide one of skill with a general dictionary of many of the terms used in this invention. Although any methods and materials similar or equivalent to those described herein can be used in the practice or testing of the present invention, the preferred methods and materials are described. Practitioners are particularly directed to Sambrook et al., 1989, and Ausubel F M et al., 1993, for definitions and terms of the art. It is to be understood that this invention is not limited to the particular methodology, protocols, and reagents described, as these may vary.

Numeric ranges are inclusive of the numbers defining the range. The term about is used herein to mean plus or minus ten percent (10%) of a value. For example, "about 100" refers to any number between 90 and 110.

Unless otherwise indicated, nucleic acids are written left to right in 5' to 3' orientation; amino acid sequences are written left to right in amino to carboxy orientation, respectively.

The headings provided herein are not limitations of the various aspects or embodiments of the invention, which can be had by reference to the specification as a whole. Accordingly, the terms defined immediately below are more fully defined by reference to the specification as a whole.

Definitions

Alpha-hemolysin: As used herein, "alpha-hemolysin," "α-hemolysin," "a-HL" and "α-HL" are used interchangeably and refer to the monomeric protein that self-assembles into a heptameric, water-filled transmembrane channel (i.e., nanopore). Depending on context, the term may also refer to the transmembrane channel formed by seven monomeric proteins.

Amino acid: As used herein, the term "amino acid," in its broadest sense, refers to any compound and/or substance that can be incorporated into a polypeptide chain. In some embodiments, an amino acid has the general structure $H_2N$—C(H)(R)—COOH. In some embodiments, an amino acid is a naturally-occurring amino acid. In some embodiments, an amino acid is a synthetic amino acid; in some embodiments, an amino acid is a D-amino acid; in some embodiments, an amino acid is an L-amino acid. "Standard amino acid" refers to any of the twenty standard L-amino acids commonly found in naturally occurring peptides.

"Nonstandard amino acid" refers to any amino acid, other than the standard amino acids, regardless of whether it is prepared synthetically or obtained from a natural source. As used herein, "synthetic amino acid" or "non-natural amino acid" encompasses chemically modified amino acids, including but not limited to salts, amino acid derivatives (such as amides), and/or substitutions. Amino acids, including carboxy- and/or amino-terminal amino acids in peptides, can be modified by methylation, amidation, acetylation, and/or substitution with other chemical without adversely affecting their activity. Amino acids may participate in a disulfide bond. The term "amino acid" is used interchangeably with "amino acid residue," and may refer to a free amino acid and/or to an amino acid residue of a peptide. It will be apparent from the context in which the term is used whether it refers to a free amino acid or a residue of a peptide. It should be noted that all amino acid residue sequences are represented herein by formulae whose left and right orientation is in the conventional direction of amino-terminus to carboxy-terminus.

Base Pair (bp): As used herein, base pair refers to a partnership of adenine (A) with thymine (T), adenine (A) with uracil (U) or of cytosine (C) with guanine (G) in a double stranded nucleic acid.

Complementary: As used herein, the term "complementary" refers to the broad concept of sequence complementarity between regions of two polynucleotide strands or between two nucleotides through base-pairing. It is known that an adenine nucleotide is capable of forming specific hydrogen bonds ("base pairing") with a nucleotide which is thymine or uracil. Similarly, it is known that a cytosine nucleotide is capable of base pairing with a guanine nucleotide.

Expression cassette: An "expression cassette" or "expression vector" is a nucleic acid construct generated recombinantly or synthetically, with a series of specified nucleic acid elements that permit transcription of a particular nucleic acid in a target cell. The recombinant expression cassette can be incorporated into a plasmid, chromosome, mitochondrial DNA, plastid DNA, virus, or nucleic acid fragment. Typically, the recombinant expression cassette portion of an expression vector includes, among other sequences, a nucleic acid sequence to be transcribed and a promoter.

Heterologous: A "heterologous" nucleic acid construct or sequence has a portion of the sequence which is not native to the cell in which it is expressed. Heterologous, with respect to a control sequence refers to a control sequence (i.e. promoter or enhancer) that does not function in nature to regulate the same gene the expression of which it is currently regulating. Generally, heterologous nucleic acid sequences are not endogenous to the cell or part of the genome in which they are present, and have been added to the cell, by infection, transfection, transformation, microinjection, electroporation, or the like. A "heterologous" nucleic acid construct may contain a control sequence/DNA coding sequence combination that is the same as, or different from a control sequence/DNA coding sequence combination found in the native cell.

Host cell: By the term "host cell" is meant a cell that contains a vector and supports the replication, and/or transcription or transcription and translation (expression) of the expression construct. Host cells for use in the present invention can be prokaryotic cells, such as *E. coli* or *Bacillus subtilus*, or eukaryotic cells such as yeast, plant, insect, amphibian, or mammalian cells. In general, host cells are prokaryotic, e.g., *E. coli*.

Lifetime: As used herein, the term "lifetime" or "nanopore lifetime" is used generally to refer to the overall length of time that a nanopore functions, in a sequencing reaction, to provide useful sequencing data. More particularly, the lifetime of a nanopore can be measured by measuring the time between the start of an experiment and when the nanopore ceases to function properly, as determined by open channel current level.

Isolated: An "isolated" molecule is a nucleic acid molecule that is separated from at least one other molecule with which it is ordinarily associated, for example, in its natural environment. An isolated nucleic acid molecule includes a nucleic acid molecule contained in cells that ordinarily express the nucleic acid molecule, but the nucleic acid molecule is present extrachromasomally or at a chromosomal location that is different from its natural chromosomal location.

Modified alpha-hemolysin: As used herein, the term "modified alpha-hemolysin" refers to an alpha-hemolysin originated from another (i.e., parental) alpha-hemolysin and contains one or more amino acid alterations (e.g., amino acid substitution, deletion, or insertion) compared to the parental alpha-hemolysin. In some embodiments, a modified alpha-hemolysin of the invention is originated or modified from a naturally-occurring or wild-type alpha-hemolysin. In some embodiments, a modified alpha-hemolysin of the invention is originated or modified from a recombinant or engineered alpha-hemolysin including, but not limited to, chimeric alpha-hemolysin, fusion alpha-hemolysin or another modified alpha-hemolysin. Typically, a modified alpha-hemolysin has at least one changed phenotype compared to the parental alpha-hemolysin.

Mutation: As used herein, the term "mutation" refers to a change introduced into a parental sequence, including, but not limited to, substitutions, insertions, deletions (including truncations). The consequences of a mutation include, but are not limited to, the creation of a new character, property, function, phenotype or trait not found in the protein encoded by the parental sequence.

Nanopore: The term "nanopore," as used herein, generally refers to a pore, channel, or passage formed or otherwise provided in a membrane. A membrane may be an organic membrane, such as a lipid bilayer, or a synthetic membrane, such as a membrane formed of a polymeric material. The membrane may be a polymeric material. The nanopore may be disposed adjacent or in proximity to a sensing circuit or an electrode coupled to a sensing circuit, such as, for example, a complementary metal-oxide semiconductor (CMOS) or field effect transistor (FET) circuit. In some examples, a nanopore has a characteristic width or diameter on the order of 0.1 nanometers (nm) to about 1000 nm. Some nanopores are proteins. Alpha-hemolysin is an example of a protein nanopore.

Nucleic Acid Molecule: The term "nucleic acid molecule" includes RNA, DNA, and cDNA molecules. It will be understood that, as a result of the degeneracy of the genetic code, a multitude of nucleotide sequences encoding a given protein such as alpha-hemolysin and/or variants thereof may be produced. The present invention contemplates every possible variant nucleotide sequence, encoding variant alpha-hemolysin, all of which are possible given the degeneracy of the genetic code.

Promoter: As used herein, the term "promoter" refers to a nucleic acid sequence that functions to direct transcription of a downstream gene. The promoter will generally be appropriate to the host cell in which the target gene is being expressed. The promoter together with other transcriptional and translational regulatory nucleic acid sequences (also termed "control sequences") are necessary to express a given gene. In general, the transcriptional and translational regulatory sequences include, but are not limited to, promoter sequences, ribosomal binding sites, transcriptional start and stop sequences, translational start and stop sequences, and enhancer or activator sequences.

Purified: As used herein, "purified" means that a molecule is present in a sample at a concentration of at least 95% by weight, or at least 98% by weight of the sample in which it is contained.

Purifying: As used herein, the term "purifying" generally refers to subjecting transgenic nucleic acid or protein containing cells to biochemical purification and/or column chromatography.

Tag: As used herein, the term "tag" refers to a detectable moiety that may be atoms or molecules, or a collection of atoms or molecules. A tag may provide an optical, electrochemical, magnetic, or electrostatic (e.g., inductive, capacitive) signature, which signature may be detected with the aid of a nanopore. Typically, when a nucleotide is attached to the tag it is called a "Tagged Nucleotide." The tag may be attached to the nucleotide via the phosphate moiety.

Time-To-Thread: The term "time to thread" or "TTT" means the time it takes the polymerase-tag complex or a nucleic acid strand to thread the tag into the barrel of the nanopore.

Variant: As used herein, the term "variant" refers to a modified protein which displays altered characteristics when compared to the parental protein, e.g., altered ionic conductance.

Variant hemolysin: The term "variant hemolysin gene" or "variant hemolysin" means, respectively, that the nucleic acid sequence of the alpha-hemolysin gene from *Staphylococcus aureus* has been altered by removing, adding, and/or manipulating the coding sequence or the amino acid sequence of the expressed protein has been modified consistent with the invention described herein.

Vector: As used herein, the term "vector" refers to a nucleic acid construct designed for transfer between different host cells. An "expression vector" refers to a vector that has the ability to incorporate and express heterologous DNA fragments in a foreign cell. Many prokaryotic and eukaryotic expression vectors are commercially available. Selection of appropriate expression vectors is within the knowledge of those having skill in the art.

Wild-type: As used herein, the term "wild-type" refers to a native gene or gene product which has the characteristics of that gene or gene product when isolated from a naturally-occurring source.

Percent homology: The term "% homology" is used interchangeably herein with the term "% identity" herein and refers to the level of nucleic acid or amino acid sequence identity between the nucleic acid sequence that encodes any one of the inventive polypeptides or the inventive polypeptide's amino acid sequence, when aligned using a sequence alignment program. For example, as used herein, 80% homology means the same thing as 80% sequence identity determined by a defined algorithm, and accordingly a homologue of a given sequence has greater than 80% sequence identity over a length of the given sequence. Exemplary levels of sequence identity include, but are not limited to, 80, 85, 90, 95, 98% or more sequence identity to a given sequence, e.g., the coding sequence for any one of the inventive polypeptides, as described herein.

Exemplary computer programs which can be used to determine identity between two sequences include, but are not limited to, the suite of BLAST programs, e.g., BLASTN, BLASTX, and TBLASTX, BLASTP and TBLASTN, publicly available on the Internet. See also, Altschul, et al., 1990 and Altschul, et al., 1997.

Sequence searches are typically carried out using the BLASTN program when evaluating a given nucleic acid sequence relative to nucleic acid sequences in the GenBank DNA Sequences and other public databases. The BLASTX program is preferred for searching nucleic acid sequences that have been translated in all reading frames against amino acid sequences in the GenBank Protein Sequences and other public databases. Both BLASTN and BLASTX are run using default parameters of an open gap penalty of 11.0, and an extended gap penalty of 1.0, and utilize the BLOSUM-62 matrix. (See, e.g., Altschul, S. F., et al., Nucleic Acids Res. 25:3389-3402, 1997.)

A preferred alignment of selected sequences in order to determine "% identity" between two or more sequences, is performed using for example, the CLUSTAL-W program in MacVector version 13.0.7, operated with default parameters, including an open gap penalty of 10.0, an extended gap penalty of 0.1, and a BLOSUM 30 similarity matrix.

Nomenclature

In the present description and claims, the conventional one-letter and three-letter codes for amino acid residues are used.

For ease of reference, variants of the application are described by use of the following nomenclature: Original amino acid(s); position(s); substituted amino acid(s). According to this nomenclature, for instance, the substitution of a glutamic acid by an asparagine in position 111 is shown as:

Glu111Asn or E111N

Multiple mutations are separated by plus signs, such as:

His35Gly+Glu111Asn or H35G+E111N representing mutations in positions 35 and 149 substituting glycine for histidine and asparagine for glutamic acid, respectively. Spans of amino acid substitutions and/or spans of residues are represented by a dash, such as a span of glycine residues from residue 126 to 131 being: 126-131Gly or 126-131G. Variations in specific substitutions are represented with a forward slash. For example, an E111N/E111S means that the E residue at position 111 may be substituted to either an N residue or S residue, respectively.

Site-Directed Mutagenesis of Alpha-Hemolysin

*Staphylococcus aureus* alpha hemolysin wild type sequences are provided herein (SEQ ID NO:1, nucleic acid coding region; SEQ ID NO:14, protein sequence) and available elsewhere (National Center for Bioinformatics or GenBank Accession Numbers M90536 and AAA26598).

Point mutations may be introduced by any method known in the art. For example, a point mutation may be made using QuikChange Lightning 2 kit (Stategene/Agilent) following manufacturer's instructions.

Primers can be ordered from commercial companies, e.g., IDT DNA.

Alpha-Hemolysin Variants

The alpha-hemolysin variants provided herein include specific substitutions—or one or more combination of substitutions—such that nanopores incorporating the variants have improved nanopore lifetime with stable, open channels during a nucleic acid sequencing reaction. By improving nanopore lifetime, sequencing reactions using such long-lifetime nanopores are able to generate more usable sequencing data over the course of a longer sequencing reaction.

In certain example embodiments, the variants include a particular mutation or series of mutations. For example, the variant may include an amino acid substitution of any one of E111N/E111S, M113A/M113S, L135I, T145S, K147N/K147S or a combination thereof of SEQ ID NO: 14. Further, in certain example embodiments, the variant may also include a H35G substitution of SEQ ID NO: 14.

Additionally, the variant may include a poly-G substitution at residues 127-129 of SEQ ID NO: 14. The variant may further include a K131G mutation. As such, in certain example embodiments, the E111N/E111S, M113A/M113S, L135I, T145S, K147N/K147S, and/or H35G substitutions described herein are accompanied by a series of poly-G amino acids at residues 126-131 of SEQ ID NO: 14. To improve nanopore stability, in certain example embodiments the alpha-hemolysin variants described herein may additionally include an amino acid substitution at H144A of SEQ ID NO: 14.

In certain example embodiments, the alpha-hemolysin variants include specific combinations of substitutions. For example, the alpha hemolysin variant may include an E111N+K147N substitution or an E111S+K147S substitution. Additionally or alternatively, the alpha-hemolysin variant may include an E111N+K147N+M113A substitution or an E111S+K147S+M113S substitution. In certain example embodiments, the alpha hemolysin variants include one of the following combinations of substitutions/residues:

E111N+126-131G+H144A+K147N;

H35G+E111N+H144A+K147N;

H35G+E111N+M113A+126-131G+H144A+K147N;

E111N+M113A+127-131G+K147N; or

E111S+M113S+T145S+K147S+L135I.

In certain example embodiments, the variant includes one or more of the substitutions described herein, while the overall sequence of the variant retains up to 80%, 85%, 90%, 95%, 98% or more sequence identity to the amino acid sequence set forth as SEQ ID NO: 2. Similarly, in other example embodiments, the variant includes one or more of the substitutions described herein, while the overall sequence of the variant retains up to 80%, 85%, 90%, 95%, 98% or more sequence identity to the amino acid sequence set forth as SEQ ID NO: 14. In certain example embodiments, the variant has 80%, 85%, 90%, 95%, 98% or more sequence identity to the amino acid sequence set forth SEQ ID NOS: 17, 18, 19, 20, or 22.

Without wishing to be bound by any particular theory, it is believed that—when a nanopore includes the variants described herein—the constriction site of the pore is widened, thereby allowing more ions to flow across the pore during a nucleic acid sequencing reaction. As a result, it is believed that nanopores including such variants have less net salt movement across the pore when the nanopore is subjected to an alternating current. By decreasing the net salt movement, the osmotic imbalance across the pore is decreased, thereby improving the overall stability of the nanopore. Hence, the resultant nanopore has an improved lifetime compared to, for example, a nanopore consisting of wild-type (native) alpha-hemolysins.

In certain example embodiments, the alpha-hemolysin variants described herein that improve nanopore lifetime may also improve Time-To-Thread during a sequencing reaction. That is, when the variant is incorporated into a nanopore, both the lifetime of the nanopore and the Time-To-Thread are improved, thus resulting in a superior nanopore. For example, any of the H35G, E111N, M113A, K147N, or 127-129G substitutions may improve both lifetime of the nanopore and Time-To-Thread. Likewise, any of the E111S, M113S, T145S, K147S, or L135I mutations may improve both lifetime of the nanopore and Time-To-Thread.

In certain example embodiments, additional substitutions may be incorporated into the variants to improve Thread-To-Thread of a resultant nanopore, thereby improving the overall functioning of the nanopore (both the lifetime and Thread-To-Thread). A list of the residues that may be mutated, for example, to improve Time-to-Thread, is provided in Table 1. In certain example embodiments, a variant resulting in improved nanopore lifetime and improved time to formed from muting one or more of the amino acids of SEQ ID NO:14 identified in Table 1 has 80%, 85%, 90%, 95%, 98% or more sequence identity to the sequence set forth as SEQ ID NO: 14. In certain example embodiments, the mutation results in the addition of a positive charge. For example, the mutation may result in a substitution of an amino acid residue identified in Table 1 to an arginine, lysine, histidine, asparagine, or other amino acid that can carry a positive charge.

In certain example embodiments, in addition to a H35G, E111N/E111S, M113A/M113S, L135I, T145S, K147N/K147S, and/or 127-129G substitution (or combination thereof) to improve nanopore lifetime, the mutation may include a particular, additional substitution to also improve Time-To-Thread. For example, the variant may additionally include an amino acid substitution of any one of V149K, E287R, T109K, P151K, or combinations thereof of SEQ ID NO: 14. In other example embodiments, the variant may include one or more these same substitutions, while the overall sequence can have up to 80%, 85%, 90%, 95%, 98% or more sequence identity to the amino acid sequence set forth as SEQ ID NO: 14. In certain example embodiments, one or more of the first 17 amino acids of SEQ ID NO: 14 mutated to either an A, N, K, or combinations thereof. Additionally or alternatively, any of the variants may include a series of glycine residue substitutions spanning from residue 127 to residue 131 of the sequence set forth as SEQ ID NO: 14, as described herein.

TABLE 1

Residues of mature alpha-hemolysin that can be mutated to form alpha-hemolysin variant.

| Position* | Residue | Position | Residue | Position | Residue | Position | Residue | Position | Residue |
|---|---|---|---|---|---|---|---|---|---|
| 1 | ALA | 65 | TYR | 124 | VAL | 175 | VAL | 229 | ALA |
| 2 | ASP | 66 | ARG | 125 | THR | 176 | ASN | 235 | ASP |
| 3 | SER | 67 | VAL | 126 | GLY | 177 | GLN | 236 | ARG |
| 4 | ASP | 68 | TYR | 127 | ASP | 178 | ASN | 237 | LYS |

TABLE 1-continued

Residues of mature alpha-hemolysin that can be mutated to form alpha-hemolysin variant.

| Position* | Residue | Position | Residue | Position | Residue | Position | Residue | Position | Residue |
|---|---|---|---|---|---|---|---|---|---|
| 5 | ILE | 69 | SER | 128 | ASP | 179 | TRP | 238 | ALA |
| 6 | ASN | 70 | GLU | 129 | THR | 180 | GLY | 239 | SER |
| 8 | LYS | 71 | GLU | 130 | GLY | 181 | PRO | 240 | LYS |
| 9 | THR | 72 | GLY | 131 | LYS | 182 | TYR | 241 | GLN |
| 10 | GLY | 73 | ALA | 132 | ILE | 183 | ASP | 244 | ASN |
| 11 | THR | 74 | ASN | 134 | GLY | 184 | ARG | 246 | ASP |
| 13 | ASP | 75 | LYS | 135 | LEU | 185 | ASP | 250 | GLU |
| 14 | ILE | 79 | ALA | 136 | ILE | 186 | SER | 252 | VAL |
| 15 | GLY | 82 | SER | 137 | GLY | 187 | TRP | 253 | ARG |
| 16 | SER | 83 | ALA | 138 | ALA | 188 | ASN | 255 | ASP |
| 17 | ASN | 85 | LYS | 139 | ASN | 189 | PRO | 257 | GLN |
| 18 | THR | 87 | GLN | 140 | VAL | 190 | VAL | 259 | HIS |
| 19 | THR | 89 | GLN | 141 | SER | 191 | TYR | 260 | TRP |
| 20 | VAL | 90 | LEU | 142 | ILE | 193 | ASN | 261 | THR |
| 21 | LYS | 91 | PRO | 143 | GLY | 194 | GLN | 262 | SER |
| 22 | THR | 92 | ASP | 144 | HIS | 197 | MET | 263 | THR |
| 24 | ASP | 93 | ASN | 145 | THR | 198 | LYS | 264 | ASN |
| 25 | LEU | 94 | GLU | 146 | LEU | 199 | THR | 266 | LYS |
| 26 | VAL | 95 | VAL | 147 | LYS | 200 | ARG | 268 | THR |
| 27 | THR | 97 | GLN | 148 | TYR | 201 | ASN | 269 | ASN |
| 28 | TYR | 102 | TYR | 149 | VAL | 202 | GLY | 270 | THR |
| 29 | ASP | 103 | PRO | 150 | GLN | 203 | SER | 271 | LYS |
| 30 | LYS | 104 | ARG | 151 | PRO | 204 | MET | 272 | ASP |
| 31 | GLU | 105 | ASN | 152 | ASP | 205 | LYS | 273 | LYS |
| 32 | ASN | 106 | SER | 153 | PHE | 207 | ALA | 274 | TRP |
| 33 | GLY | 107 | ILE | 154 | LYS | 208 | ASP | 275 | THR |
| 35 | HIS | 108 | ASP | 155 | THR | 210 | PHE | 276 | ASP |
| 36 | LYS | 109 | THR | 156 | ILE | 211 | LEU | 277 | ARG |
| 37 | LYS | 110 | LYS | 158 | GLU | 212 | ASP | 278 | SER |
| 40 | TYR | 111 | GLU | 159 | SER | 213 | PRO | 280 | GLU |
| 44 | ASP | 112 | TYR | 160 | PRO | 214 | ASN | 281 | ARG |
| 45 | ASP | 113 | MET | 161 | THR | 215 | LYS | 282 | TYR |
| 46 | LYS | 114 | SER | 162 | ASP | 216 | ALA | 283 | LYS |
| 47 | ASN | 115 | THR | 163 | LYS | 218 | SER | 285 | ASP |
| 48 | HIS | 116 | LEU | 164 | LYS | 221 | SER | 286 | TRP |
| 49 | ASN | 117 | THR | 168 | LYS | 222 | SER | 287 | GLU |
| 50 | LYS | 118 | TYR | 170 | ILE | 224 | PHE | 288 | LYS |
| 51 | LYS | 120 | PHE | 171 | PHE | 225 | SER | 289 | GLU |
| 56 | ARG | 121 | ASN | 172 | ASN | 226 | PRO | 291 | MET |
| 62 | ALA | 122 | GLY | 173 | ASN | 227 | ASP | 292 | THR |
| 64 | GLN | 123 | ASN | 174 | MET | 228 | PHE | 293 | ASN |

*Position corresponds to the specific amino acid position in SEQ ID NO: 14.

While the α-hemolysin variant can include various combinations of substitutions as described herein, in certain example embodiments the α-hemolysin variant incudes particular combinations of substitutions to improve Time-to-Thread. For example, an α-hemolysin variant may include the following combinations of amino acid substitutions of the sequence set forth as SEQ ID NO: 14:

H35G+V149K;

V149K+E287R+H35G;

V149K+E287R;

T109K+H35G;

P151K+H35G;

V149K+P151K+H35G;

T109K+V149K+H35G;

V149K+K147N+E111N+127-131G+M113A+H35G;

V149K+K147N+E111N+127-131G+M113A; or,

T109K+V149K+P151K+H35G.

Such combinations may also include, for example, a substitution at H144A of SEQ ID NO: 14 and/or a series of glycine residues at amino acids 127-131 of SEQ ID NO: 14. In certain example embodiments, the α-hemolysin variant includes an amino acid sequence having at least 80%, 90%, 95%, 98%, or more sequence identity to the amino acid sequence set forth as SEQ ID NO: 4, SEQ ID NO: 5, SEQ ID NO: 6, SEQ ID NO: 7, SEQ ID NO: 8, SEQ ID NO: 9, SEQ ID NO: 10, SEQ ID NO: 11, SEQ ID NO: 12, or SEQ ID NO: 13, with the substitution(s) identified in each sequence, for example, being preserved in the variant.

In certain example embodiments, the amino acid substitution described herein allows the addition of heterologous molecules, such as polyethylene glycol (PEG). In certain example aspects, the a-HL variant has one or more post-translational modifications. In certain example aspects, the substitution is a non-native amino acid that is basic or positively charged at a pH from about 5 to about 8.5.

In certain example embodiments, the amino acids forming all or a part of the variants described herein may be stereoisomers. Additionally or alternatively, the amino acids forming all or a part of the variants described herein may be modifications of naturally occurring amino acids, non-naturally occurring amino acids, post-translationally modified amino acids, enzymatically synthesized amino acids, derivatized amino acids, constructs or structures designed to mimic amino acids, and the like. The amino acids forming the variants described herein may be one or more of the 20 common amino acids found in naturally occurring proteins, or one or more of the modified and unusual amino acids. In certain example embodiments, the amino acids may be D- or L-amino acids.

In certain example embodiments, the variants may also include one or more modified amino acids. The modified amino acid may be a derivatized amino acid or a modified and unusual amino acid. Examples of modified and unusual amino acids include but are not limited to, 2-Aminoadipic acid (Aad), 3-Aminoadipic acid (Baad), β-Amino-propionic acid (Bala, β-alanine), 2-Aminobutyric acid (Abu, piperidinic acid), 4-Aminobutyric acid (4Abu), 6-Aminocaproic acid (Acp), 2-Aminoheptanoic acid (Ahe), 2-Aminoisobutyric acid (Aib), 3-Aminoisobutyric acid (Baib), 2-Aminopimelic acid (Apm), 2,4-Diaminobutyric acid (Dbu), Desmosine (Des), 2,2'-Diaminopimelic acid (Dpm), 2,3-Diaminopropionic acid (Dpr), N-Ethylglycine (EtGly), N-Ethylasparagine (EtAsn), Hydroxylysine (Hyl), allo-Hydroxylysine (AHyl), 3-Hydroxyproline (3Hyp), 4-Hydroxyproline (4Hyp), Isodesmosine (Ide), alto-Isoleucine (AIle), N-Methylglycine (MeGly, sarcosine), N-Methylisoleucine (MeIle), 6-N-Methyllysine (MeLys), N-Methylvaline (MeVal), Norvaline (Nva), Norleucine (Nle), and Ornithine (Orn). Other examples of modified and unusual amino acids are described generally in Synthetic Peptides: A User's Guide, Second Edition, April 2002, Edited Gregory A. Grant, Oxford University Press; Hruby V J, Al-obeidi F and Kazmierski W: Biochem J 268:249-262, 1990; and Toniolo C: *Int J Peptide Protein Res* 35:287-300, 1990; the teachings of all of which are expressly incorporated herein by reference.

In certain example embodiments, the amino acid sequence of the variant is sequential, without any modified and unusual amino acids interrupting the sequence of D- or L-amino acids. In other embodiments, the sequence may include one or more modified and unusual amino acids as noted above. For example, the sequence of the variant may be interrupted by one or more modified and unusual amino acids. Accordingly, provided are pseudopeptides and peptidomimetics, including structures that have a non-peptidic backbone. In certain example embodiments, the variants include dimers or multimers of peptides.

So that the variants and WT alpha-hemolysin can be manipulated, in certain example embodiments any of the amino acid sequences described herein, such as those set forth as SEQ ID NO: 4-14, and 17-20, and 22, may also include a linker sequences or affinity tags, and further may include sequences for removing such tags (e.g., protease cleavage sites). For example, in some embodiments of the amino acid sequences described herein, the sequences may include a linker/TEV/HisTAG sequence at the C-terminal end having the sequence GLSA<u>ENLYFQ</u>GHHHHHH (SEQ ID NO: 16, where the TEV sequence is underlined). As those skilled in the art will appreciate, such a sequence allows for the purification of the variant.

Nanopore Assembly and Insertion

The alpha-hemolysin peptides described herein can be assembled into a multimeric protein assembly (i.e., a nanopore). Hence, the resultant nanopore will include multiple, alpha-hemolysin subunits. For example, a heptameric alpha-hemolysin nanopore includes seven subunits.

Any of the alpha-hemolysin variants described herein can be used in nanopore assembly. The subunits of a given nanopore, for example, can be identical copies of the same polypeptide or they can be different polypeptides. For example, each of the seven subunits of a heptameric assembly may have an amino acid sequence corresponding to the amino acid sequence set forth as SEQ ID NOS: 17, 18, 19, 20, or 22. In other example embodiments, the subunits may include the substitutions identified in SEQ ID NOS: 17, 18, 19, 20, or 22, but may only have 80%, 85%, 90%, 95%, 98% or more sequence identity to the amino acid sequence set forth as SEQ ID NOS: 17, 18, 19, 20, or 22, respectively.

In other example embodiments, each of the subunits may include the same series of substitutions, with one or more of each of subunits of the nanopore having a different overall amino acid sequence. That is, while a particular substitution or combination of substitutions may be conserved among all subunits in a given nanopore, the overall amino acid sequences of the various subunits may be different. In certain example embodiments, a nanopore including variant alpha-hemolysin subunits that are the same or substantially the same provide an improved lifetime as compared to a nanopore having a mixture of different alpha-hemolysin subunits. For example, a nanopore including only alpha-hemolysin variant subunits having 80%, 85%, 90%, 95%, 98% or more sequence identity to one of the amino acid sequence set forth as SEQ ID NOS: 17, 18, 19, 20, or 22 may have a greater lifetime than a nanopore that includes variant subunits along with wild-type (native) subunits.

In certain example embodiments, one or more of the subunits may additionally include substitutions that improve Time-To-Thread as described herein. Hence, resultant nanopore has both improved lifetime and increased Time-to-Thread. In certain example embodiments, the nanopore may include a mixture of the variants described herein and other alpha-hemolysin polypeptides, such as wild-type (native) alpha-hemolysins. In certain example embodiments, the nanopores have a defined ratio of modified subunits (e.g., a-HL variants) to un-modified subunits (e.g., a-HL). In certain example embodiments and as described further below, the nanopore has a polymerase attached to one of the subunits to form a nanopore assembly.

Also provided herein are methods for producing multimeric proteins (e.g., nanopores or nanopore assemblies) having a defined ratio of modified subunits to un-modified subunits. With reference to FIG. 27 of WO2014/074727, a method for assembling a protein having a plurality of subunits includes providing a plurality of first subunits 2705 and providing a plurality of second subunits 2710, where the second subunits are modified when compared with the first subunits. In some cases, the first subunits are wild-type (e.g., purified from native sources or produced recombinantly). The second subunits can be modified in any suitable way. In some cases, the second subunits have a protein (e.g., a polymerase) attached (e.g., as a fusion protein).

In certain example embodiments, the modified subunits can comprise a chemically reactive moiety (e.g., an azide or an alkyne group suitable for forming a linkage). In some cases, the method further comprises performing a reaction (e.g., a Click chemistry cycloaddition) to attach an entity (e.g., a polymerase) to the chemically reactive moiety.

In certain example embodiments, the method can further include contacting the first subunits with the second subunits 2715 in a first ratio to form a plurality of proteins 2720 having the first subunits and the second subunits. For example, one part modified aHL subunits having a reactive group suitable for attaching a polymerase can be mixed with six parts wild-type aHL subunits (i.e., with the first ratio being 1:6). The plurality of proteins can have a plurality of ratios of the first subunits to the second subunits. For example, the mixed subunits can form several nanopores having a distribution of stoichiometries of modified to un-modified subunits (e.g., 1:6, 2:5, 3:4).

In certain example embodiments, the proteins are formed by simply mixing the subunits. In the case of aHL nanopores for example, a detergent (e.g., deoxycholic acid) can trigger the aHL monomer to adopt the pore conformation. The nanopores can also be formed, for example, using a lipid (e.g., 1,2-diphytanoyl-sn-glycero-3-phosphocholine (DPhPC) or 1,2-di-0-phytanyl-sn-glycero-3-phosphocholine (DoPhPC)) and moderate temperature (e.g., less than about 100° C.). In some cases, mixing DPhPC with a buffer solution creates large multi-lamellar vesicles (LMV), and adding aHL subunits to this solution and incubating the mixture at 40° C. for 30 minutes results in pore formation.

If two different types of subunits are used (e.g., the natural wild type protein and a second aHL monomer which can contain a single point mutation), the resulting proteins can have a mixed stoichiometry (e.g., of the wild type and mutant proteins). The stoichiometry of these proteins can, in certain example embodiments, follow a formula which is dependent upon the ratio of the concentrations of the two proteins used in the pore forming reaction. This formula is as follows:

$$100 P_m = 100[n!/m!(n-m)!] \cdot f_{mut}^m \cdot f_{wt}^{n-m}, \text{ where}$$

$P_m$=probability of a pore having m number of mutant subunits n=total number of subunits (e.g., 7 for aHL)
m=number of "mutant" subunits
$f_{mut}$=fraction or ratio of mutant subunits mixed together
$f_{wt}$=fraction or ratio of wild-type subunits mixed together The method can further comprise fractionating the plurality of proteins to enrich proteins that have a second ratio of the first subunits to the second subunits 2725. For example, nanopore proteins can be isolated that have one and only one modified subunit (e.g., a second ratio of 1:6). However, any second ratio is suitable. A distribution of second ratios can also be fractionated such as enriching proteins that have either one or two modified subunits. The total number of subunits forming the protein is not always 7 (e.g., a different nanopore can be used or an alpha-hemolysin nanopore can form having six subunits) as depicted in FIG. 27 of WO2014/074727. In some embodiments, proteins having only one modified subunit are enriched. In such cases, the second ratio is 1 second subunit per (n−1) first subunits where n is the number of subunits comprising the protein.

The first ratio can be the same as the second ratio, however this is not required. In some embodiments, proteins having mutated monomers can form less efficiently than those not having mutated subunits. If this is the case, the first ratio can be greater than the second ratio (e.g., if a second ratio of 1 mutated to 6 non-mutated subunits are desired in a nanopore, forming a suitable number of 1:6 proteins may require mixing the subunits at a ratio greater than 1:6).

Proteins having different second ratios of subunits can behave differently (e.g., have different retention times) in a separation. In certain example embodiments, the proteins are fractionated using chromatography, such as ion exchange chromatography or affinity chromatography. Since the first and second subunits can be identical apart from the modification, the number of modifications on the protein can serve as a basis for separation. In some cases, either the first or second subunits have a purification tag (e.g., in addition to the modification) to allow or improve the efficiency of the fractionation. In some embodiments, a poly-histidine tag (His-tag), a streptavidin tag (Strep-tag), or other peptide tag is used. In some embodiments, the first and second subunits each comprise different tags and the fractionation step fractionates on the basis of each tag. In the case of a His-tag, a charge is created on the tag at low pH (Histidine residues become positively charged below the pKa of the side chain). With a significant difference in charge on one of the aHL molecules compared to the others, ion exchange chromatography can be used to separate the oligomers which have 0, 1, 2, 3, 4, 5, 6, or 7 of the "charge-tagged" aHL subunits. In principle, this charge tag can be a string of any amino acids which carry a uniform charge. FIG. 28 and FIG. 29 show examples of fractionation of nanopores based on a His-tag. FIG. 28 shows a plot of ultraviolet absorbance at 280 nanometers, ultraviolet absorbance at 260 nanometers, and conductivity. The peaks correspond to nanopores with various ratios of modified and unmodified subunits. FIG. 29 of WO2014/074727 shows fractionation of aHL nanopores and mutants thereof using both His-tag and Strep-tags.

In certain example embodiments, an entity (e.g., a polymerase) is attached to the protein following fractionation. The protein can be a nanopore protein and the entity can be a polymerase. In some instances, the method further comprises inserting the proteins having the second ratio subunits into a bilayer.

As described herein, a nanopore can comprise a plurality of subunits. A polymerase can be attached to one of the subunits and at least one and less than all of the subunits comprise a first purification tag. In some instances, all of the subunits comprise a first purification tag or a second purification tag. The first purification tag can, for example, be a poly-histidine tag (e.g., on the subunit having the polymerase attached).

Attachment of Polymerase to Nanopore

As described herein, a polymerase (e.g., DNA polymerase) is attached to and/or is located in proximity to the nanopore. Any DNA polymerase capable of synthesizing DNA during a DNA synthesis reaction may be used in accordance with the methods and compositions described herein. Example DNA polymerases include, but are not limited to, phi29 (*Bacillus bacteriophage* φ29), pol6 (*Clostridium phage* phiCPV4; GenBank: AFH27113.1) or pol7 (*Actinomyces phage* Av-1; GenBank: ABR67671.1). In certain example embodiments, attached to the nanopore assembly is a DNA-manipulating or modifying enzyme, such as a ligase, nuclease, phosphatase, kinase, transferase, or topoisomerase.

In certain example embodiments, the polymerase is a polymerase variant. For example, the polymerase variant may include any of the polymerase variants identified in U.S. patent application Ser. No. 15/012,317 (published as the US 2016/0222363 A1, also referred to herein as the "'317 Application"). Such variants include, for example, one or more amino acid substitutions at H223A, N224Y/L, Y225L/T/I/F/A, H227P, I295 W/F/M/E, Y342L/F, T343N/F, I357G/L/Q/H/W/M/A/E/Y/P, S360G, L361M/W/V, I363V, S365Q/W/M/A/G, S366A/L, Y367L/E/M/P/N, P368G, D417P, E475D, Y476V, F478L, K518Q, H527 W/R/L, T529M/F, M531H/Y/A/K/R/W/T/L/V, N535L/Y/M/K/I, G539Y/F, P542E/S, N545K/D/S/L/R, Q546 W/F, A547M/Y/W/F/V/S, L549Q/Y/H/G/R, I550A/W/T/G/F/S, N552L/M/S, G553S/T, F558P/T, A596S, G603T, A610T/E, V615A/T, Y622A/M, C623G/S/Y, D624F, I628Y/V/F, Y629W/H/M, R632L/C, N635D, M641 L/Y, A643L, I644H/M/Y, T647G/A/E/K/S, I648K/R/V/N/T, T651Y/F/M, I652Q/G/S/N/F/T, K655G/F/E/N, W656E, D657R/P/A, V658L, H660A/Y, F6621/L, L690M, or combinations thereof of SEQ ID NO: 15 (which corresponds to SEQ ID NO: 2 of the '317 Application). In certain example embodiments, the polymerase includes one or more such substitutions and has 80%, 90%, 95%, 98% or more sequence identity to the amino acid sequence set forth as SEQ ID NO: 15. As described in the '317 Application, the polymerase variant may have altered enzyme activity, fidelity, processivity, elongation rate, sequencing accuracy, long continuous read capability, stability, or solubility relative to the parental polymerase.

The polymerase can be attached to the nanopore assembly in any suitable way known in the art. See, for example, PCT/US2013/068967 (published as WO2014/074727; Genia Technologies), PCT/US2005/009702 (published as WO2006/028508), and PCT/US2011/065640 (published as WO2012/083249; Columbia Univ). In certain example embodiments, the polymerase is attached to the nanopore (e.g., hemolysin) protein monomer and then the full nanopore heptamer is assembled (e.g., in a ratio of one monomer with an attached polymerase to 6 nanopore (e.g., hemolysin) monomers without an attached polymerase). The nanopore heptamer can then be inserted into the membrane.

Another method for attaching a polymerase to a nanopore involves attaching a linker molecule to a hemolysin monomer or mutating a hemolysin monomer to have an attachment site and then assembling the full nanopore heptamer (e.g., at a ratio of one monomer with linker and/or attachment site to 6 hemolysin monomers with no linker and/or attachment site). A polymerase can then be attached to the attachment site or attachment linker (e.g., in bulk, before inserting into the membrane). The polymerase can also be attached to the attachment site or attachment linker after the (e.g., heptamer) nanopore is formed in the membrane. In some cases, a plurality of nanopore-polymerase pairs are inserted into a plurality of membranes (e.g., disposed over the wells and/or electrodes) of the biochip. In some instances, the attachment of the polymerase to the nanopore complex occurs on the biochip above each electrode.

The polymerase can be attached to the nanopore with any suitable chemistry (e.g., covalent bond and/or linker). In some cases, the polymerase is attached to the nanopore with molecular staples. In some instances, molecular staples comprise three amino acid sequences (denoted linkers A, B and C). Linker A can extend from a hemolysin monomer, Linker B can extend from the polymerase, and Linker C then can bind Linkers A and B (e.g., by wrapping around both Linkers A and B) and thus the polymerase to the nanopore. Linker C can also be constructed to be part of Linker A or Linker B, thus reducing the number of linker molecules.

In certain example embodiments, the polymerase is linked to the nanopore using Solulink™ chemistry. Solulink™ can be a reaction between HyNic (6-hydrazino-nicotinic acid, an aromatic hydrazine) and 4FB (4-formylbenzoate, an aromatic aldehyde). In some instances, the polymerase is linked to the nanopore using Click chemistry (available from LifeTechnologies for example). In some cases, zinc finger mutations are introduced into the hemolysin molecule and then a molecule is used (e.g., a DNA intermediate molecule) to link the polymerase to the zinc finger sites on the hemolysin.

Additionally or alternatively, the SpyTag/SpyCatcher system, which spontaneously forms covalent isopeptide linkages under physiological conditions, may be used to join an alpha-hemolysin monomer to the polymerase. See, for example, Li et al, J Mol Biol. 2014 Jan. 23; 426(2):309-17. For example, an alpha-hemolysin protein can be expressed having a SpyTag domain. Further, the DNA polymerase to be joined to the alpha-hemolysin may be separately expressed as fusion protein having a SpyCatcher domain. By mixing the alpha-hemolysin/SpyTag fusion protein with the DNA Polymerase/SpyCatcher protein, the SpyTag and SpyCatcher proteins interact to form the alpha-hemolysin monomer that is linked to a DNA polymerase via a covalent isopeptide linkage. In certain example embodiments, the SpyTag domain is attached to the alpha-hemolysin via a linker sequence. For example, the linker-SpyTag protein may include the sequence GGSSGGSSGGAHIVMVDAYKPTK (SEQ ID NO: 21), with the underlined portion being the linker sequence and the bolded portion being the SpyTag sequence. In certain example embodiments, a HisTag is attached to the SpyTag sequence of the SpyTag sequence. For example, the HisTag may be linked to the SpyTag via a KG linker.

In certain example embodiments, the polymerase may be attached to a nanopore monomer before the nanopore monomer is incorporated into a nanopore assembly. For example, following expression and purification of the alpha-hemolysin/SpyTag fusion protein, the purified alpha-hemolysin/SpyTag fusion protein is mixed with purified polymerase/SpyCatcher fusion protein, thus allowing the SpyTag and SpyCatcher proteins bind each other to form an alpha-hemolysin/polymerase monomer. The monomer can then be incorporated into the nanopore assembly as described herein to form a heptameric assembly.

In certain example embodiments, the polymerase is attached to the nanopore assembly after formation of the nanopore assembly. For example, following expression and purification of the alpha-hemolysin/SpyTag fusion protein, the fusion protein is incorporated into the nanopore assembly to form the heptameric nanopore assembly. The polymerase/SpyCatcher fusion protein is then mixed with the heptameric assembly, thus allowing the SpyTag and SpyCatcher proteins bind each other, which in turn results in binding of the polymerase to the nanopore assembly.

Because of the nature of nanopore-based sequencing reaction, those skilled in the art will appreciate that it is beneficial to have only a single polymerase associated with each nanopore assembly (rather than multiple polymerases). To achieve such assemblies, the nanopore assembly may be configured, for example, to have only a single SpyTag, which therefore allows the attachment of a single polymerase/SpyCatcher.

In the case of alpha-hemolysin, for example, mixing the alpha-hemolysin/SpyTag proteins with additional alpha-hemolysin proteins results in heptamers having 0, 1, 2, 3, 4, 5, 6, or 7 alpha-hemolysin/SpyTag subunits. Yet because of the different number of SpyTag sequences (0, 1, 2, 3, 4, 5, 6, or 7) associated with each heptamer, the heptamers have different charges. Hence, in certain example embodiments, the heptamers can be separated by methods known in the art, such as via elution with cation exchange chromatography. The eluted fractions can then be examined to determine which fraction includes an assembly with a single SpyTag. The fraction with a single SpyTag can then be used to attach a single polymerase to each assembly, thereby creating a nanopore assemblies with a single polymerase attached thereto.

While a variety of methods may be suitable for determining which heptamer fraction contains a single SpyTag (and that is hence capable of binding a only single polymerase/SpyCatcher fusion protein per heptamer), in certain example embodiments the different heptamer fraction can be separated based on molecular weight, such as via SDS-PAGE. A reagent can then be used to confirm the presence of SpyTag associated with each fraction. For example, a SpyCatcher- GFP (green fluorescent protein) can be added to the fractions before separation via SDS-PAGE.

Because heptamers with fewer numbers of SpyTags are smaller than the heptamers with greater number of SpyTags, the fraction with a single SpyTag can be identified, as evidenced by the furthest band migration and the presence of GFP fluorescence in the SDS-PAGE gel corresponding to the band. For example, a fraction containing seven alpha-hemolysin monomers and zero SpyTag fusion proteins will migrate the furthest, but will not fluoresce when mixed with SpyCatcher-GFP because of the absence of the SpyTag bound to the heptamers. The fraction containing a single SpyTag, however, will both migrate the next furthest (compared to other fluorescent bands) and will fluoresce, thereby allowing identification of the fraction with a single SpyTag bound to the heptamer. Following identification of the fraction with a single SpyTag bound to the heptamer, the polymerase/SpyCatcher fusion protein can then be added to this fraction, thereby linking the polymerase to the nanopore assembly.

By using the methods and compositions described herein, a nanopore assembly tethered to a single DNA polymerase—and including one or more of the alpha hemolysin variants as described herein—can be achieved. For example, a heptameric nanopore may include seven variant subunits, with each subunit having a sequence corresponding to one of the amino acid sequence set forth in SEQ ID NOS: 17, 18, 19, 20, or 22 or to an amino acid sequence that is, respectively, 80%, 85%, 90%, 95%, 98% or more identical thereto, with a DNA polymerase attached to one of the subunits.

Apparatus Set-Up

The nanopore described herein may be formed or otherwise embedded in a membrane disposed adjacent to a sensing electrode of a sensing circuit, such as an integrated circuit. The integrated circuit may be an application specific integrated circuit (ASIC). In some examples, the integrated circuit is a field effect transistor or a complementary metal-oxide semiconductor (CMOS). The sensing circuit may be situated in a chip or other device having the nanopore, or off of the chip or device, such as in an off-chip configuration. The semiconductor can be any semiconductor, including, without limitation, Group IV (e.g., silicon) and Group III-V semiconductors (e.g., gallium arsenide). See, for example, WO 2013/123450, for the apparatus and device set-up for sensing a nucleotide or tag.

Pore based sensors (e.g., biochips) can be used for electro-interrogation of single molecules. A pore based sensor can include a nanopore of the present disclosure formed in a membrane that is disposed adjacent or in proximity to a sensing electrode. The sensor can include a counter electrode. The membrane includes a trans side (i.e., side facing the sensing electrode) and a cis side (i.e., side facing the counter electrode).

In certain example embodiments, a nanopore including one or more of the alpha-hemolysin variants described herein, will have an improved nanopore lifetime relative to a nanopore including wild-type alpha-hemolysin (i.e., a nanopore without any of the substitutions described herein). In certain example embodiments, the greater the number of variants included in the nanopore corresponds to a greater level of improvement in nanopore lifetime. For example, a heptameric nanopore where each of the seven alpha-hemolysin subunits corresponds to one of the sequences set forth as SEQ ID NOS: 17, 18, 19, 20, or 22 or a sequence that is, respectively, 80%, 85%, 90%, 95%, 98% or more identical thereto, may have a longer lifetime than a nanopore including only wild-type (native) alpha-hemolysin or fewer than seven variants. That is, in certain example embodiments, the greater of number of variants included in the nanopore corresponds to a longer nanopore lifetime. In certain example embodiments, all seven of the subunits of a heptameric nanopore include substitutions, such as the same substitution or overlapping substitutions that improve nanopore lifetime. The variants in a given nanopore may be the same variant or a combination of different variants.

In certain example embodiments, the lifetime of a nanopore including one or more alpha-hemolysin variants as described herein, such as those provided in SEQ ID NOS: 17, 18, 19, 20, and 22, is increased by about 5%, 10%, 20%, 30%, 40%, 50%, 60%, 70%, 80% or more as compared to a nanopore including only wild-type (native) alpha-hemolysin. In certain example embodiments, the lifetime of a nanopore including one or more alpha-hemolysin variants as described herein is doubled or tripled as compared to a nanopore including only wild-type (native) alpha-hemolysin.

In certain example embodiments, in addition to an improved nanopore lifetime, the time for a tag to thread through the pore (the time-to-thread or TTT) may be decreased. For example, the TTT for a nanopore comprising one or more of the variants described herein may be decreased by about 10%, 20%, 30%, 40%, 50%, 60%, 70%, 80% or more as compared to a heptameric nanopore assembly consisting of wild-type (native) alpha-hemolysin. As such, a nanopore including one or more of the variants described herein may having an increased lifetime of 5%, 10%, 20%, 30%, 40%, 50%, 60%, 70%, 80% or more—as well as a decreased TTT of 5%, 10%, 20%, 30%, 40%, 50%, 60%, 70%, 80% or more—as compared to a heptameric nanopore assembly consisting of wild-type (native) alpha-hemolysin.

In the experimental disclosure that follows, the following abbreviations apply: eq (equivalents); M (Molar); µM (micromolar); N (Normal); mol (moles); mmol (millimoles); µmol (micromoles); nmol (nanomoles); g (grams); mg (milligrams); kg (kilograms); µg (micrograms); L (liters); ml (milliliters); µl (microliters); cm (centimeters); mm (millimeters); µm (micrometers); nm (nanometers); ° C. (degrees Centigrade); h (hours); min (minutes); sec (seconds); msec (milliseconds).

EXAMPLES

The present invention is described in further detain in the following examples which are not in any way intended to limit the scope of the invention as claimed. The attached Figures are meant to be considered as integral parts of the specification and description of the invention. All references cited are herein specifically incorporated by reference for all that is described therein. The following examples are offered to illustrate, but not to limit the claimed invention.

Example 1

Expression and Recovery

This example illustrates the expression and recovery of protein from bacterial host cells, e.g., *E. coli*.

DNA encoding the wild-type a-HL was purchased from a commercial source. The sequence was verified by sequencing.

Plasmid construction. The gene encoding either a wild-type or variant α-hemolysin was inserted into a pPR-IBA2 plasmid (IBA Life Sciences, Germany) under the control of T7 promoter.

Transformation. E. coli BL21 DE3 (from Life Technologies) cells were transformed with the expression vector comprising the DNA encoding the wild-type or variant α-hemolysin using techniques well-known in the art. Briefly, the cells were thawed on ice (if frozen). Next, the desired DNA (in a suitable vector/plasmid) was added directly into the competent cells (should not exceed 5% of that of the competent cells) and mixed by flicking the tube. The tubes were placed on ice for 20 minutes. Next, the cells were placed in a 42° C. water bath for 45 seconds without mixing, followed by placing the tubes on ice for 2 min. The cells were then transferred to a 15 ml sterilized culture tube containing 0.9 ml of SOC medium (pre-warmed at room temperature) and cultured at 37° C. for 1 hr in a shaker. Finally, an aliquot of the cells were spread onto a LB agar plate containing the appropriate antibiotic and the plates incubated at 37° C. overnight.

Protein Expression. Following transformation, colonies were picked and inoculated into a small volume (e.g., 3 ml) of growth medium (e.g., LB broth) containing the appropriate antibiotic with shaking at 37° C., overnight.

The next morning, transfer 1 ml of the overnight culture to a new 100 ml of autoinduction medium, e.g., Magic Media (Life Technologies) containing an appropriate antibiotic to select the expression plasmid. Grow the culture with shaking at 25° C. approximately 16 hrs but this depended on the expression plasmids. Cells were harvested by centrifugation at 3,000 g for 20 min at 4° C. and stored at −80° C. until used.

Purification. Cells were lysed via sonication. The alpha-hemolysin was purified to homogeneity by affinity column chromatography.

Example 2

Alpha-Hemolysin Variants

The following example details the introduction of a mutation at a desired residue.

Mutations. Site-directed mutagenesis is carried out using a QuikChange Multi Site-Directed Mutagenesis kit (Stratagene, La Jolla, Calif.) to prepare the example H35G+V149K+H144A (SEQ ID NO: 4) and H35G+E111N+M113A+126-131G+H144A+K147N (SEQ ID NO: 19), with the sequences including a C-terminal linker/TEV/HisTag for purification. QuikChange Multi Site-Directed Mutagenesis kit (Stratagene, La Jolla, Calif.) is also carried out to prepare a variant (E111N+M113A+126-131G+K147N, SEQ ID NO: 20) for Polymerase attachment, with the variant including a C-terminal SpyTag, KG linker, and HisTag. The variants were expressed and purified as in Example 1.

Example 3

Assembly of Nanopore Including Variants

This example describes the assembly of a 1:6 heptameric nanopore including one subunit having a SpyTag sequence for subsequent polymerase attachment (the "α-HL-variant-SpyTag" subunit) and six α-HL-variant subunits with no SpyTag (the "α-HL-variant" subunits).

The α-HL-variant-SpyTag (E111N+M113A+126-131G+K147N, SEQ ID NO: 20)) was prepared and expressed as described in Examples 1 and 2 with a C-terminal SpyTag, KG linker, and HisTag, The α-HL-variant-SpyTag protein was then then purified on a cobalt affinity column using a cobalt elution buffer (200 mM NaCl, 300 mM imidazole, 50 mM tris, pH 8). The protein was stored at 4° C. if used within 5 days, otherwise 8% trehalose was added and stored at −80° C.

For the α-HL-variant subunits, variants of H35G+E111N+M113A+126-131G+H144A+K147N (SEQ ID NO: 19) were prepared and expressed as described in Examples 1 and 2 with a linker/TEV/HisTag and purified on a cobalt affinity column using a cobalt elution buffer (200 mM NaCl, 300 mM imidazole, 50 mM tris, pH 8). The α-HL-variant protein was then incubated with 1 mg of TEV protease for every 5 mg of protein at 4 C for 4 hours. After incubation with TEV protease the mixture is purified on a cobalt affinity column to remove TEV protease and undigested protein. The proteins were stored at 4° C. if used within 5 days, otherwise 8% trehalose was added and stored at −80° C.

Using approximately 10 mg of total protein, the α-HL-variant-SpyTag to desired α-HL-variant protein solutions were mixed together at a 1:9 ratio to ultimately facilitate the formation of a mixture of heptamers at the desired ratio. It is expected that such a mixture heptamers will result in various fractions that include varying ratios of α-HL-variant-SpyTag to α-HL-variant protein (0:7; 1:6, 2:5, 3:4, etc.), where the α-HL-variant-SpyTag component is present as 0, 1, 2, 3, 4, 5, 6, or seven monomeric subunits of the heptamer.

Diphytanoylphosphatidylcholine (DPhPC) lipid was solubilized in either 50 mM Tris, 200 mM NaCl, pH 8 or 150 mM KCl, 30 mM HEPES, pH 7.5 to a final concentration of 50 mg/ml and added to the mixture of α-HL monomers to a final concentration of 5 mg/ml. The mixture of the α-HL monomers was incubated at 37° C. for at least 60 min. Thereafter, n-Octyl-β-D-Glucopyranoside (βOG) was added to a final concentration of 5% (weight/volume) to solubilize the resulting lipid-protein mixture. The sample was centrifuged to clear protein aggregates and left over lipid complexes and the supernatant was collected for further purification.

The mixture of α-HL heptamers was then subjected to cation exchange purification and the elution fractions collected. For each fraction, two samples were prepared for SDS-PAGE. The first sample included 15 uL of α-HL eluate alone and the second sample was combined with 3 ug of SpyCatcher-GFP. The samples were then incubated and sheltered from light and at room temperature for 1-16 hours. Following incubation, 5 uL of 4× Laemmli SDS-PAGE buffer (Bio-Rad™) was added to each sample. The samples and a PrecisionPlus™ Stain-Free protein ladder were then loaded onto a 4-20% Mini-PROTEAN Stain-Free protein precast gel (Bio-Rad). The gels were run at 200 mV for 30 minutes. The gels were then imaged using a Stain-Free filter.

The conjugation of SpyCatcher-GFP to heptameric α-HL/SpyTag can be observed through molecular weight band shifts during SDS-PAGE. Heptamers containing a single SpyTag will bind a single SpyCatcher-GFP molecular and will thus have a shift that corresponds to the molecular weight of the heptameric pore plus the molecular weight of a single SpyCatcher-GFP, while heptamers with two or more SpyTags should have correspondingly larger molecular weight shifts. Therefore, the peaks eluted off of the cation exchange column during heptameric α-HL purification above can be analyzed for the ratio of α-HL/SpyTag to α-HL-variant. In addition, the presence of SpyCatcher-GFP attachment can be observed using a GFP-fluorescence filter when imaging the SDS-PAGE gels.

Based on this rationale, the fraction whose molecular weight shift corresponded to a single addition of SpyCatcher-GFP was determined using a molecular weight standard protein ladder. Bio-Rad's stain-free imaging system was used to determine the molecular weight shift. The presence of GFP fluorescence was determined using a blue filter. The presence of fluorescence was used to confirm the presence of the SpyTag protein. The elution fraction corresponding to the 1:6 ratio, i.e., one α-HL-variant-SpyTag to six α-HL-variants, was then used for further experiments.

Using these same or similar procedures, a 1:6 heptamer was also produced having a V149K substitution added to each of the H35G+E111N+M113A+126-131G+H144A+K147N (SEQ ID NO: 19) α-HL-variants. That is, the "six" component of the 1:6 heptamer included a V149K substitution, with the α-HL-variant-SpyTag "one" component being E111N+M113A+126-131G+K147N denoted as N rectification in Table 2 (SEQ ID NO: 20).

In addition to the 1:6 heptamers described above, these same or similar procedures were used to create a 1:6 heptamer having six H35G+V149K+H144A (SEQ ID NO: 4) α-HL-variants. More particularly, such 1:6 heptamers have a wild-type α-HL-SpyTag as the "one" component of the 1:6 ratio and a "six" component including six H35G+V149K+H144A (SEQ ID NO: 4) α-HL-variants.

Example 4

Attachment of a Polymerase

This example provides for the attachment of a polymerase to a nanopore.

The polymerase may be coupled to the nanopore by any suitable means. See, for example, PCT/US2013/068967 (published as WO2014/074727; Genia Technologies), PCT/US2005/009702 (published as WO2006/028508), and PCT/US2011/065640 (published as WO2012/083249; Columbia Univ).

The polymerase, e.g., phi29 DNA Polymerase, was coupled to a protein nanopore (e.g. alpha-hemolysin), through a linker molecule. Specifically, the SpyTag and SpyCatcher system, which spontaneously forms covalent isopeptide linkages under physiological conditions, was used. See, for example, Li et al, J Mol Biol. 2014 Jan. 23; 426(2):309-17.

Briefly, the Sticky phi29 SpyCatcher HisTag was expressed according to Example 1 and purified using a cobalt affinity column. The SpyCatcher polymerase and the SpyTag oligomerized protein were incubated at a 1:1 molar ratio overnight at 4° C. in 3 mM SrCl$_2$. The 1:6-polymerase-template complex is then purified using size-exclusion chromatography.

Example 5

Activity of the Variants

This example shows the activity of the nanopores as provided by Examples 1-4 (nanopores with an attached polymerase).

The variant nanopores were assayed to determine the effect of the substitutions. More particularly, the 1:6 ratio nanopores with the "one" component of the nanopore including the α-HL-variant-SpyTag (with the polymerase attached) and the "six" component including the α-HL-variants were assayed to determine the effect of the substitutions on nanopore lifetime. Nanopores also including the V149K substitution were similarly assayed to determined nanopore lifetime (see Table 2, below). Further, nanopores having the 1:6 wild-type α-HL-SpyTag (with polymerase attached) as the "one" component and six H35G+V149K+H144A (SEQ ID NO: 4) α-HL-variants as the "six" component were analyzed for the effect of the substitutions on Time-To-Thread.

To perform the assays, the bilayers were formed and pores were inserted as described in PCT/US14/61853 filed 23 Oct. 2014. The nanopore device (or sensor) used to detect a molecule (and/or sequence a nucleic acid) was set-up as described in WO2013123450.

Assessment of Nanopore Lifetime

This assay was designed to measure the time a nanopore is able to function properly in a lipid bilayer under the effect of alternating voltages, i.e., squarewaves.

Figure 2A:
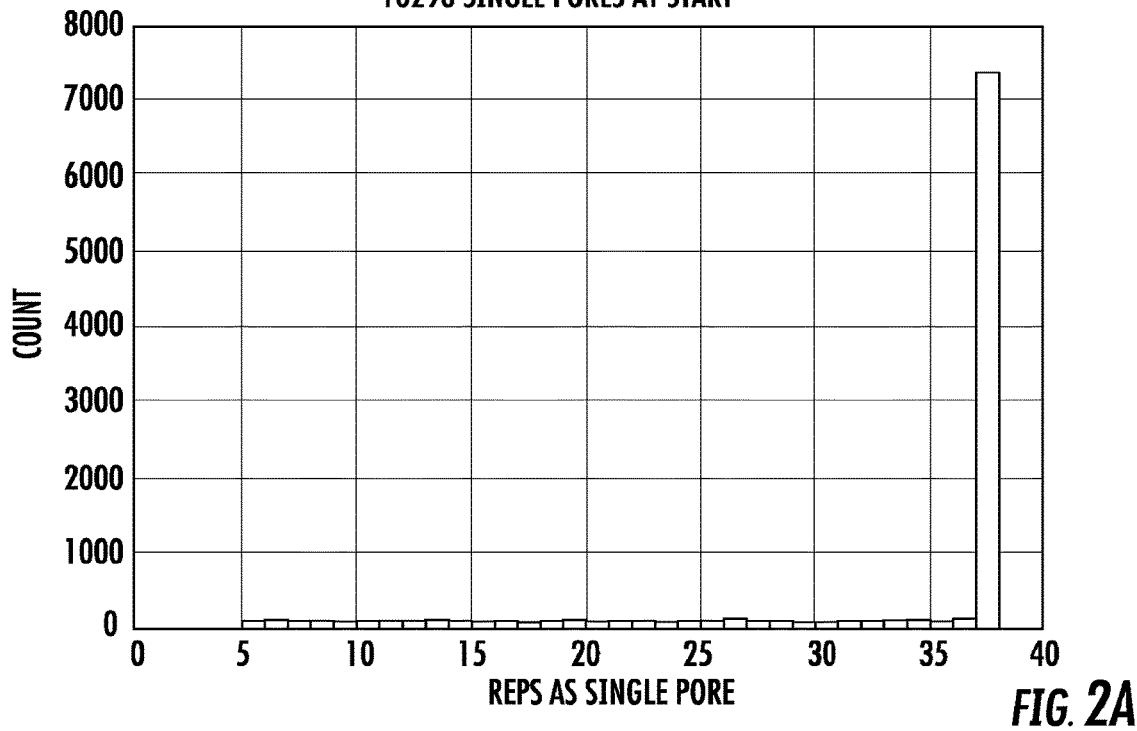
FIG. 2A is a histogram showing lifetime assessment for an N Rectification nanopore. The y-axis is the number of pores which had a lifetime within the bin on the x-axis. The x-axis is the number of 100s intervals (reps) in which the current passing through the channel corresponded to that of a single N Rectification Hemolysin nanopore. This experiment was run for 3600s, or 36 reps.
Figure 2B:
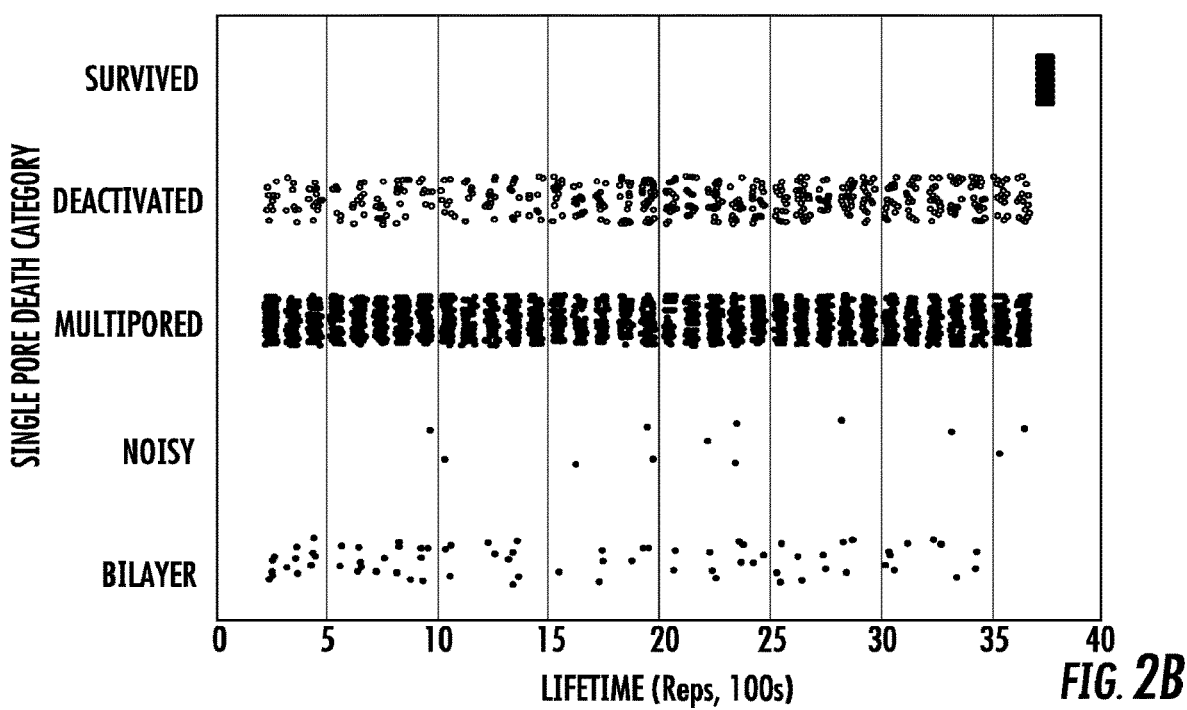
FIG. 2B is a graph showing an analysis of the failure mechanisms of the N Rectification nanopore for the same run as FIG. 2A. This experiment was run for 3600s, or 36 reps. represents an analysis of the failure mechanisms of the nanopore for the same run as FIG. 1A. In this depiction, individual pores are displayed as dots in a number of categories. The first category is for those pores which survived until the end of the experiment; their mode of failure was that the instrument was shut off. The second category is for cells that were turned off by the Genia FPGA because the current increased very quickly to a level >10× of the current of a single nanopore, which is a general indicator that the lipid bilayer was disrupted. The third category is for when the open channel current increases from that of a single pore to that of a multiple of a single pore, but lower than 10× the current. This typically indicates that 2, 3, 4, 5, 6, 7, 8, or 9 nanopores inserted into the bilayer that originally only harbored one. The noisy bin contains pores where some unknown mode of failure occurred, which typically results in an unstable level of current is being measured; this may be due to electrode failure. The last category is bilayer, and corresponds to the situation where current is no longer measured passing through a nanopore, but rather the characteristically low conductance of a lipid bilayer is seen.
Figure 3A:
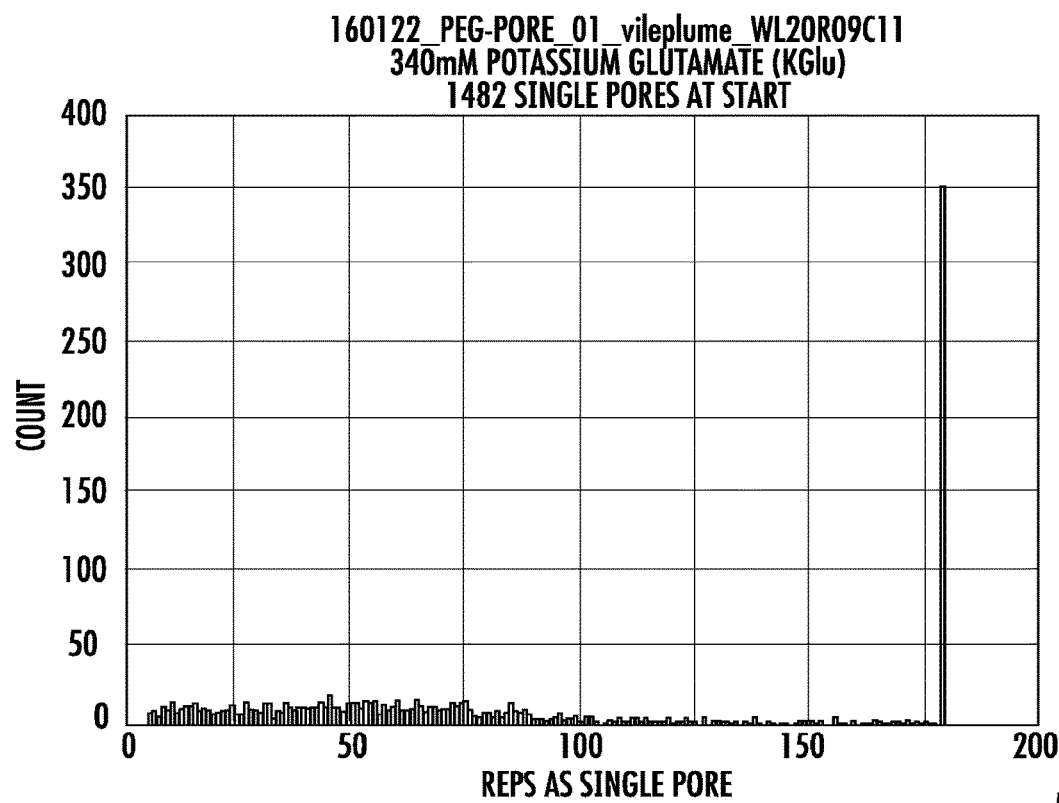
FIG. 3A is a histogram showing lifetime assessment for an N Rectification nanopore. The y-axis is the number of pores which had a lifetime within the bin on the x-axis. The x-axis is the number of 100s intervals (reps) in which the current passing through the channel corresponded to that of a single N Rectification Hemolysin nanopore. This experiment was run for 18000s, or 180 reps.
Figure 3B:
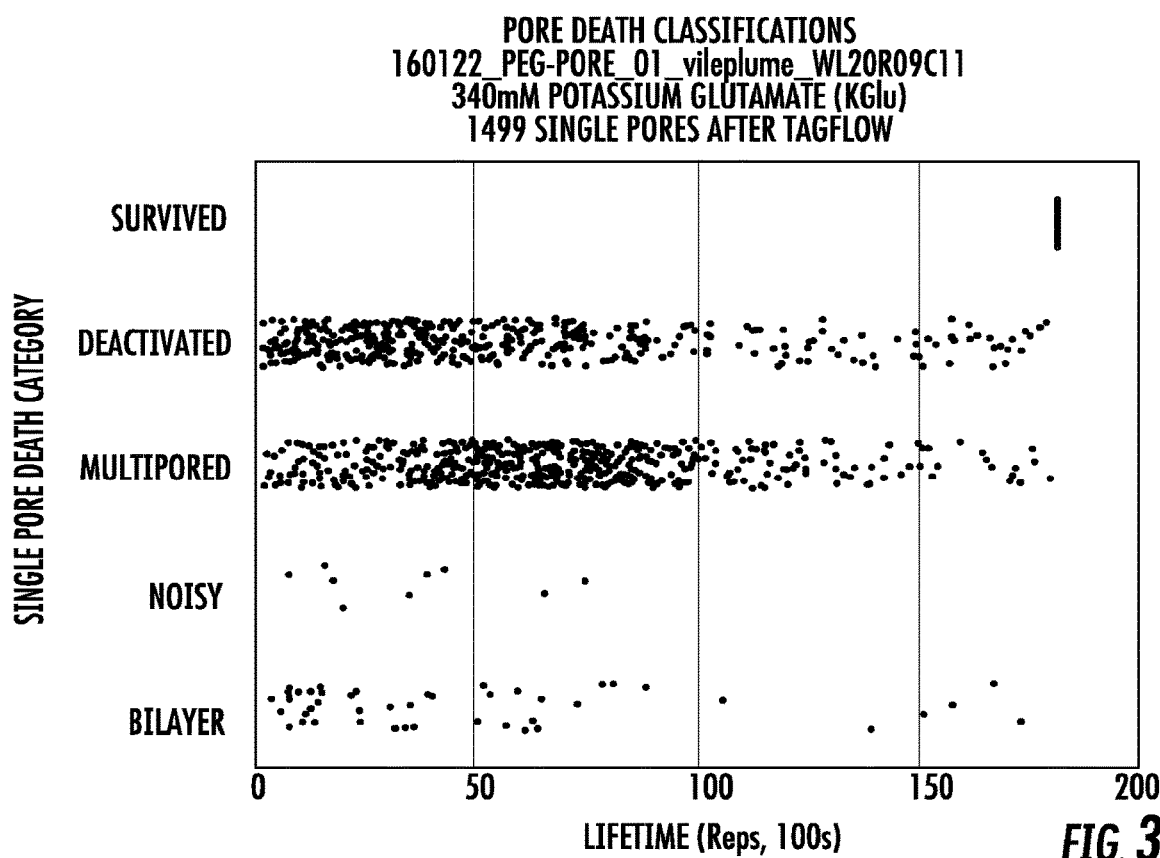
FIG. 3B is a graph showing an analysis of the failure mechanisms of the N Rectification nanopore for the same run as FIG. 3A. This experiment was run for 3600s, or 36 reps. represents an analysis of the failure mechanisms of the nanopore for the same run as FIG. 1A. In this depiction, individual pores are displayed as dots in a number of categories. The first category is for those pores which survived until the end of the experiment; their mode of failure was that the instrument was shut off. The second category is for cells that were turned off by the Genia FPGA because the current increased very quickly to a level >10× of the current of a single nanopore, which is a general indicator that the lipid bilayer was disrupted. The third category is for when the open channel current increases from that of a single pore to that of a multiple of a single pore, but lower than 10× the current. This typically indicates that 2, 3, 4, 5, 6, 7, 8, or 9 nanopores inserted into the bilayer that originally only harbored one. The noisy bin contains pores where some unknown mode of failure occurred, which typically results in an unstable level of current is being measured; this may be due to electrode failure. The last category is bilayer, and corresponds to the situation where current is no longer measured passing through a nanopore, but rather the characteristically low conductance of a lipid bilayer is seen.

To measure the nanopore lifetime we have devised an assay that uses alternating positive and negative voltages (squarewaves) to pore lifetime. Our sequencing complex is comprised of a protein nanopore (αHL) which is attached to a single DNA polymerase (see Example 4). Current passes differently through the pore in the positive and negative applied voltages. Nanopores may pass ions differently under positive compared to negative voltages. This leads to a pumping of salt and water ions out of the well. Over the lifetime of the pore, this process gradually deforms the bilayer, and causes the nanopore to no longer conduct ions across the bilayer. When this happens, it marks the end of the pore lifetime. These times are then recorded and plotted as a histogram, as shown in FIG. 1A, FIG. 2A, and FIG. 3A.

To carry out the "lifetime" assay, the Genia Sequencing device is used with a Genia Sequencing Chip. The electrodes are conditioned and phospholipid bilayers are established on the chip as explained in PCT/US2013/026514. Genia's sequencing complex is inserted to the bilayers following the protocol described in PCT/US2013/026514 (published as WO2013/123450). The pore lifetime data was collected using a buffer system comprised of 20 mM HEPES pH 8, 300 mM KGlu, 3 uM tagged nucleotide, 3 mM Mg$^{2+}$, with a voltage applied of 235 mV peak to peak with a modulation rate of 80 Hz.

As shown in FIGS. 1A-1B, 2A-2B, and 3A-3B, nanopores including 1:6 ratios of α-HL-variant-SpyTag (E111N+M113A+126-131G+K147N, SEQ ID NO: 20) and α-HL-variant subunits (H35G+E111N+M113A+126-131G+H144A+K147N (SEQ ID NO: 19)) showed significantly improved lifetimes. And, while addition V149K substitution did reduce the overall level of improved lifetime of the nanopores, the lifetime was nevertheless improved by 5.4% to ~26% of pores lasting at least 1 hour (as compared to controls) (see Table 2).

| Pore Type | Pore Concentration on Chip (μM) | Buffer Conditions (mM KGlu) | Average Percent of Single Pores that Lasted at Least 1 Hour |
|---|---|---|---|
| H144A* | -- enriched | 300/380 | 17.9 |
| V149K* | -- enriched | 300/380 | 13.4 |
| N Rectification | 0.0001 | 380/380 | 88 |
| V149K + N Rectification | 0.001 | 380/380 | 5.4 |
| V149K + N Rectification | 0.0001 | 380/380 | 27.8 |
| V149K + N Rectification | 0.00005 | 380/380 | 24.7 |

Table 2—Assessment of V149K on improved nanopore lifetime. Briefly, Different pore types were tested for both Time-to-Thread and Pore Lifetime under different conditions. E111N+M113A+126-131G+K147N are referred to as "N Rectification" in order to conserve space. N Rectification pores have a longer pore lifetime than their H144A or V149K counterparts. When V149K and N Rectification mutations are combined, the resulting mutant has >2x the pore lifetime of V149K alone when diluted to 0.0001 uM.

Assessment of Time-to-Thread

This assay was designed to measure the time it takes to capture a tagged molecule by a DNA polymerase attached to the nanopore using alternating voltages, i.e., squarewaves.

To measure the time it takes to capture a tagged nucleotide by a DNA polymerase in our sequencing complex we have devised an assay that uses alternating positive and negative voltages (squarewaves) to determine the amount of time this takes. Our sequencing complex is comprised of a protein nanopore (αHL) which is attached to a single DNA polymerase (see Example 4). The tagged nucleotides are negatively charged, and are therefore attracted to the nanopore when the voltage applied is positive in nature, and repelled when the voltage applied to the nanopore sequencing complex is negative. So we can measure the time it takes for a tag to thread into the pore by cycling the voltage between positive and negative potentials and determine how much time the nanopore's current is unobstructed (open channel) verses when the tag is threaded (reduced current flux).

To carry out the "time-to-thread" assay, the Genia Sequencing device is used with a Genia Sequencing Chip. The electrodes are conditioned and phospholipid bilayers are established on the chip as explained in PCT/US2013/026514. Genia's sequencing complex is inserted to the bilayers following the protocol described in PCT/US2013/026514 (published as WO2013/123450). The time-to-thread data was collected using a buffer system comprised of 20 mM HEPES pH 8, 300 mM KGlu, 3 uM tagged nucleotide, 3 mM $Mg^{2+}$, with a voltage applied of 235 mV peak to peak with a duty cycle of 80 Hz.

After the data was collected, it was analyzed for squarewaves that showed the capture of a tagged nucleotide (threaded level) which lasted to the end of the positive portion of the squarewave, and was followed by another tag capture on the subsequent squarewave. The time-to-thread was measured by determining how long the second squarewave reported unobstructed open channel current. As an example, if 10 consecutive squarewaves showed tagged nucleotide captures that lasted to the end of the positive portion of the squarewave then the time-to-thread parameter would be calculated from squarewaves 2-10 (the first squarewave does not factor into the calculation because the polymerase did not have a tag bound to it in the previous squarewave). These time-to-thread numbers were then collected for all of the pores in the experiment and statistical parameters extracted from them (such as a mean, median, standard deviation etc.).

Figure 4A:
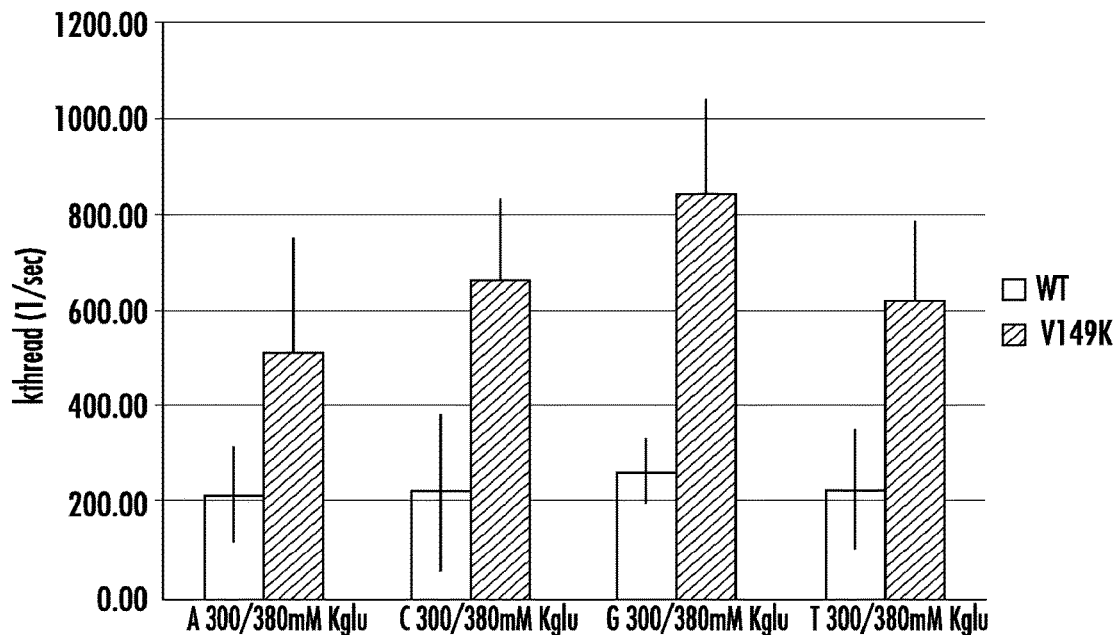
FIG. 4A is a graph showing the time-to-thread for control heptameric nanopores as compared to heptameric nanopores including one alpha-hemolysin/phi29 DNA Polymerase conjugate and six alpha-hemolysin variants, each variant having substitutions at H35G+V149K+H144A (i.e., a 1:6 ratio), as set forth in SEQ ID NO: 4. The control nanopores (labeled "WT") include a 1:6 ratio of alpha-hemolysin/phi29 DNA Polymerase conjugate to six wild-type alpha-hemolysins. These data are combined from many pores which were capturing the tagged nucleotides indicating the pore had both a polymerase and a template DNA molecule. As shown for each tag (corresponding to A, C, G, T), the threading rate for a nanopore including the variant alpha hemolysin was significantly increased compared to the control nanopore, thus evidencing an improved (decreased) time-to-thread. In the case of the C-nucleotide tag the threading rate increased from a mean value of 221.62 $s^{-1}$ (standard deviation 13.6 $s^{-1}$) to 663.15 (standard deviation 172 $s^{-1}$). Other nucleotide tags showed similar increases as shown in FIG. 1.
Figure 4B:
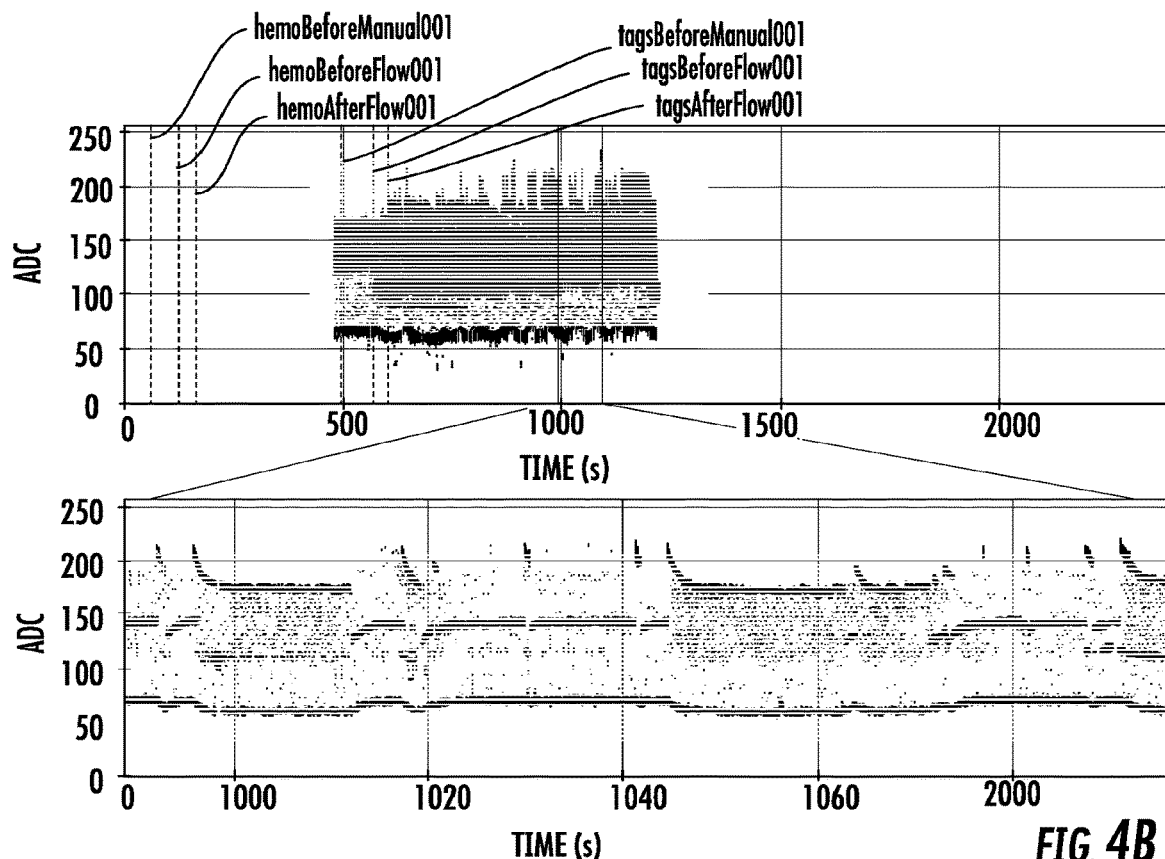
FIG. 4B is a graph showing the raw data used to generate FIG. 4A.

Results for the H35G+V149K+H144A variant, as compared to controls, are shown in FIGS. 4A-4B.

It is understood that the examples and embodiments described herein are for illustrative purposes only and that various modifications or changes in light thereof will be suggested to persons skilled in the art and are to be included within the spirit and purview of this application and scope of the appended claims. All publications, patents, and patent applications cited herein are hereby incorporated by reference in their entirety for all purposes.

The sequences disclosed in this application are set forth as follows:

```
                    SEQUENCE LISTING FREE TEXT

SEQ ID NO: 1 (WT aHL DNA)
ATGGCAGATC TCGATCCCGC GAAATTAATA CGACTCACTA TAGGGAGGCC     50
ACAACGGTTT CCCTCTAGAA ATAATTTTGT TTAACTTTAA GAAGGAGATA    100
TACAAATGGA TTCAGATATT AATATTAAAA CAGGTACAAC AGATATTGGT    150
TCAAATACAA CAGTAAAAAC TGGTGATTTA GTAACTTATG ATAAAGAAAA    200
TGGTATGCAT AAAAAAGTAT TTTATTCTTT TATTGATGAT AAAAATCATA    250
ATAAAAAATT GTTAGTTATT CGTACAAAAG GTACTATTGC AGGTCAATAT    300
AGAGTATATA GTGAAGAAGG TGCTAATAAA AGTGGTTTAG CATGGCCATC    350
TGCTTTTAAA GTTCAATTAC AATTACCTGA TAATGAAGTA GCACAAATTT    400
CAGATTATTA TCCACGTAAT AGTATTGATA CAAAAGAATA TATGTCAACA    450
TTAACTTATG GTTTTAATGG TAATGTAACA GGTGATGATA CTGGTAAAAT    500
TGGTGGTTTA ATTGGTGCTA ATGTTTCAAT TGGTCATACA TTAAAATATG    550
TACAACCAGA TTTTAAAACA ATTTTAGAAA GTCCTACTGA TAAAAAAGTT    600
GGTTGGAAAG TAATTTTTAA TAATATGGTT AATCAAAATT GGGGTCCTTA    650
TGATCGTGAT AGTTGGAATC CTGTATATGG TAATCAATTA TTTATGAAAA    700
CAAGAAATGG TTCTATGAAA GCAGCTGATA ATTTCTTAGA TCCAAATAAA    750
GCATCAAGTT TATTATCTTC AGGTTTTTCT CCTGATTTTG CAACAGTTAT    800
TACTATGGAT AGAAAAGCAT CAAAACAACA AACAAATATT GATGTTATTT    850
ATGAACGTGT AAGAGATGAT TATCAATTAC ATTGGACATC AACTAATTGG    900
AAAGGTACAA ATACTAAAGA TAAATGGACA GATAGAAGTT CAGAAAGATA    950
TAAAATTGAT TGGGAAAAAG AAGAAATGAC AAATGGTCTC AGCGCTTGGA   1000
GCCACCCGCA GTTCGAAAAA TAA 1023

SEQ ID NO: 2 (WT aHL amino acids) [as expressed in E. coli]
MADSDINIKT GTTDIGSNTT VKTGDLVTYD KENGMHKKVF YSFIDDKNHN     50
KKLLVIRTKG TIAGQYRVYS EEGANKSGLA WPSAFKVQLQ LPDNEVAQIS    100
DYYPRNSIDT KEYMSTLTYG FNGNVTGDDT GKIGGLIGAN VSIGHTLKYV    150
QPDFKTILES PTDKKVGWKV IFNNMVNQNW GPYDRDSWNP VYGNQLFMKT    200
RNGSMKAADN FLDPNKASSL LSSGFSPDFA TVITMDRKAS KQQTNIDVIY    250
ERVRDDYQLH WTSTNWKGTN TKDKWTDRSS ERYKIDWEKE EMTNGLSAWS    300
HPQFEK                                                   306

SEQ ID NO: 3 (Mature WT aHL, with purification tag)
ADSDINIKTG TTDIGSNTTV KTGDLVTYDK ENGMHKKVFY SFIDDKNHNK     50
KLLVIRTKGT IAGQYRVYSE EGANKSGLAW PSAFKVQLQL PDNEVAQISD    100
YYPRNSIDTK EYMSTLTYGF NGNVTGDDTG KIGGLIGANV SIGHTLKYVQ    150
PDFKTILESP TDKKVGWKVI FNNMVNQNWG PYDRDSWNPV YGNQLFMKTR    200
NGSMKAADNF LDPNKASSLL SSGFSPDFAT VITMDRKASK QQTNIDVIYE    250
RVRDDYQLHW TSTNWKGTNT KDKWTDRSSE RYKIDWEKEE MTNGLSAWSH    300
```

| SEQUENCE LISTING FREE TEXT |
| --- |

PQFEK                                                              305

SEQ ID NO: 4 (H35G+V149K+H144A)
ADSDINIKTG TTDIGSNTTV KTGDLVTYDK ENGMGKKVFY SFIDDKNHNK    50
KLLVIRTKGT IAGQYRVYSE EGANKSGLAW PSAFKVQLQL PDNEVAQISD        100
YYPRNSIDTK EYMSTLTYGF NGNVTGDDTG KIGGLIGANV SIGATLKYKQ    150
PDFKTILESP TDKKVGWKVI FNNMVNQNWG PYDRDSWNPV YGNQLFMKTR        200
NGSMKAADNF LDPNKASSLL SSGFSPDFAT VITMDRKASK QQTNIDVIYE        250
RVRDDYQLHW TSTNWKGTNT KDKWTDRSSE RYKIDWEKEE MTN 293

SEQ ID NO: 5 (H35G+H144A+V149K+E287R)
ADSDINIKTG TTDIGSNTTV KTGDLVTYDK ENGMGKKVFY SFIDDKNHNK    50
KLLVIRTKGT IAGQYRVYSE EGANKSGLAW PSAFKVQLQL PDNEVAQISD        100
YYPRNSIDTK EYMSTLTYGF NGNVTGDDTG KIGGLIGANV SIGATLKYKQ    150
PDFKTILESP TDKKVGWKVI FNNMVNQNWG PYDRDSWNPV YGNQLFMKTR        200
NGSMKAADNF LDPNKASSLL SSGFSPDFAT VITMDRKASK QQTNIDVIYE        250
RVRDDYQLHW TSTNWKGTNT KDKWTDRSSE RYKIDWRKEE MTN 293

SEQ ID NO: 6 (V149K+E287R)
ADSDINIKTG TTDIGSNTTV KTGDLVTYDK ENGMGKKVFY SFIDDKNHNK        50
KLLVIRTKGT IAGQYRVYSE EGANKSGLAW PSAFKVQLQL PDNEVAQISD        100
YYPRNSIDTK EYMSTLTYGF NGNVTGDDTG KIGGLIGANV SIGHTLKYKQ        150
PDFKTILESP TDKKVGWKVI FNNMVNQNWG PYDRDSWNPV YGNQLFMKTR        200
NGSMKAADNF LDPNKASSLL SSGFSPDFAT VITMDRKASK QQTNIDVIYE        250
RVRDDYQLHW TSTNWKGTNT KDKWTDRSSE RYKIDWRKEE MTN 293

SEQ ID NO: 7 (T109K+H35G)
ADSDINIKTG TTDIGSNTTV KTGDLVTYDK ENGMGKKVFY SFIDDKNHNK        50
KLLVIRTKGT IAGQYRVYSE EGANKSGLAW PSAFKVQLQL PDNEVAQISD        100
YYPRNSIDKK EYMSTLTYGF NGNVTGDDTG KIGGLIGANV SIGATLKYKQ    150
PDFKTILESP TDKKVGWKVI FNNMVNQNWG PYDRDSWNPV YGNQLFMKTR        200
NGSMKAADNF LDPNKASSLL SSGFSPDFAT VITMDRKASK QQTNIDVIYE        250
RVRDDYQLHW TSTNWKGTNT KDKWTDRSSE RYKIDWRKEE MTN 293

SEQ ID NO: 8 (P151K+H35G)
ADSDINIKTG TTDIGSNTTV KTGDLVTYDK ENGMGKKVFY SFIDDKNHNK    50
KLLVIRTKGT IAGQYRVYSE EGANKSGLAW PSAFKVQLQL PDNEVAQISD        100
YYPRNSIDKK EYMSTLTYGF NGNVTGDDTG KIGGLIGANV SIGATLKYVQ    150
KDFKTILESP TDKKVGWKVI FNNMVNQNWG PYDRDSWNPV YGNQLFMKTR    200
NGSMKAADNF LDPNKASSLL SSGFSPDFAT VITMDRKASK QQTNIDVIYE        250
RVRDDYQLHW TSTNWKGTNT KDKWTDRSSE RYKIDWEKEE MTN 293

SEQ ID NO: 9 (V149K+P151K+H35G)
ADSDINIKTG TTDIGSNTTV KTGDLVTYDK ENGMGKKVFY SFIDDKNHNK    50
KLLVIRTKGT IAGQYRVYSE EGANKSGLAW PSAFKVQLQL PDNEVAQISD        100
YYPRNSIDTK EYMSTLTYGF NGNVTGDDTG KIGGLIGANV SIGATLKYKQ    150
KDFKTILESP TDKKVGWKVI FNNMVNQNWG PYDRDSWNPV YGNQLFMKTR    200
NGSMKAADNF LDPNKASSLL SSGFSPDFAT VITMDRKASK QQTNIDVIYE        250
RVRDDYQLHW TSTNWKGTNT KDKWTDRSSE RYKIDWEKEE MTN 293

SEQ ID NO: 10 (T109K+V149K+H35G)
ADSDINIKTG TTDIGSNTTV KTGDLVTYDK ENGMGKKVFY SFIDDKNHNK    50
KLLVIRTKGT IAGQYRVYSE EGANKSGLAW PSAFKVQLQL PDNEVAQISD        100
YYPRNSIDKK EYMSTLTYGF NGNVTGDDTG KIGGLIGANV SIGATLKYKQ    150
PDFKTILESP TDKKVGWKVI FNNMVNQNWG PYDRDSWNPV YGNQLFMKTR        200
NGSMKAADNF LDPNKASSLL SSGFSPDFAT VITMDRKASK QQTNIDVIYE        250
RVRDDYQLHW TSTNWKGTNT KDKWTDRSSE RYKIDWEKEE MTN 293

SEQ ID NO: 11 (V149K+K147N+E111N+127-131G+M113A+H35G)
ADSDINIKTG TTDIGSNTTV KTGDLVTYDK ENGMGKKVFY SFIDDKNHNK        50
KLLVIRTKGT IAGQYRVYSE EGANKSGLAW PSAFKVQLQL PDNEVAQISD        100
YYPRNSIDTK NYASTLTYGF NGNVTGGGG GIGGLIGANV SIGATLNYKQ    150
PDFKTILESP TDKKVGWKVI FNNMVNQNWG PYDRDSWNPV YGNQLFMKTR        200
NGSMKAADNF LDPNKASSLL SSGFSPDFAT VITMDRKASK QQTNIDVIYE        250
RVRDDYQLHW TSTNWKGTNT KDKWTDRSSE RYKIDWEKEE MTN 293

SEQ ID NO: 12 (VI49K+K147N+E111N+127-131G+M113A)
ADSDINIKTG TTDIGSNTTV KTGDLVTYDK ENGMHKKVFY SFIDDKNHNK        50
KLLVIRTKGT IAGQYRVYSE EGANKSGLAW PSAFKVQLQL PDNEVAQISD        100
YYPRNSIDTK NYASTLTYGF NGNVTGGGG GIGGLIGANV SIGATLNYKQ    150
PDFKTILESP TDKKVGWKVI FNNMVNQNWG PYDRDSWNPV YGNQLFMKTR        200
NGSMKAADNF LDPNKASSLL SSGFSPDFAT VITMDRKASK QQTNIDVIYE        250
RVRDDYQLHW TSTNWKGTNT KDKWTDRSSE RYKIDWEKEE MTN 293

SEQ ID NO: 13 (T109K+V149K+P151K+H35G)
ADSDINIKTG TTDIGSNTTV KTGDLVTYDK ENGMGKKVFY SFIDDKNHNK    50
KLLVIRTKGT IAGQYRVYSE EGANKSGLAW PSAFKVQLQL PDNEVAQISD        100

| SEQUENCE LISTING FREE TEXT |
|---|

```
YYPRNSIDKK EYMSTLTYGF NGNVTGDDTG KIGGLIGANV SIGATLKYKQ    150
KDFKTILESP TDKKVGWKVI FNNMVNQNWG PYDRDSWNPV YGNQLFMKTR    200
NGSMKAADNF LDPNKASSLL SSGFSPDFAT VITMDRKASK QQTNIDVIYE    250
RVRDDYQLHW TSTNWKGTNT KDKWTDRSSE RYKIDWEKEE MTN           293

SEQ ID NO: 14 (Mature WT aHL; AAA26598)
ADSDINIKTG TTDIGSNTTV KTGDLVTYDK ENGMHKKVFY SFIDDKNHNK    50
KLLVIRTKGT IAGQYRVYSE EGANKSGLAW PSAFKVQLQL PDNEVAQISD    100
YYPRNSIDTK EYMSTLTYGF NGNVTGDDTG KIGGLIGANV SIGHTLKYVQ    150
PDFKTILESP TDKKVGWKVI FNNMVNQNWG PYDRDSWNPV YGNQLFMKTR    200
NGSMKAADNF LDPNKASSLL SSGFSPDFAT VITMDRKASK QQTNIDVIYE    250
RVRDDYQLHW TSTNWKGTNT KDKWTDRSSE RYKIDWEKEE MTN           293

SEQ ID NO: 15 (Pol6 with His Tag)
MHHHHHHHS GGSDKHTQYV KEHSFNYDEY KKANFDKIEC LIFDTESCTN     50
YENDNTGARV YGWGLGVTRN HNMIYGQNLN QFWEVCQNIF NDWYHDNKHT    100
IKITKTKKGF PKRKYIKFPI AVHNLGWDVE FLKYSLVENG FNYDKGLLKT    150
VFSKGAPYQT VTDVEEPKTF HIVQNNNIVY GCNVYMDKFF EVENKDGSTT    200
EIGLCLDFFD SYKIITCAES QFHNYVHDVD PMFYKMGEEY DYDTWRSPTH    250
KQTTLELRYQ YNDIYMLREV IEQFYIDGLC GGELPLTGMR TASSIAFNVL    300
KKMTFGEEKT EEGYINYFEL DKKTKFEFLR KRIEMESYTG GYTHANHKAV    350
GKTINKIGCS LDINSSYPSQ MAYKVFPYGK PVRKTWGRKP KTEKNEVYLI    400
EVGFDFVEPK HEEYALDIFK IGAVNSKALS PITGAVSGQE YFCTNIKDGK    450
AIPVYKELKD TKLTTNYNW LTSVEYEFWI KHFNFGVFKK DEYDCFEVDN     500
LEFTGLKIGS ILYYKAEKGK FKPYVDHFTK MKVENKKLGN KPLTNQAKLI    550
LNGAYGKFGT KQNKEEKDLI MDKNGLLTFT GSVTEYEGKE FYRPYASFVT    600
AYGRLQLWNA IIYAVGVENF LYCDTDSIYC NREVNSLIED MNAIGETIDK    650
TILGKWDVEH VFDKFKVLGQ KKYMYHDCKE DKTDLKCCGL PSDARKIIIG    700
QGFDEFYLGK NVEGKKQRKK VIGGCLLLDT LFTIKKIMF*              739

SEQ ID NO: 16 (Linker/TEV/HisTag (TEV portion underlined))
GLSAENLYFQGHHHHHH

SEQ ID NO: 17 (E111N+126-131G+H144A+K147N)
ADSDINIKTG TTDIGSNTTV KTGDLVTYDK ENGMHKKVFY SFIDDKNHNK    50
KLLVIRTKGT IAGQYRVYSE EGANKSGLAW PSAFKVQLQL PDNEVAQISD    100
YYPRNSIDTK NYMSTLTYGF NGNVTGGGGG GIGGLIGANV SIGATLNYVQ    150
PDFKTILESP TDKKVGWKVI FNNMVNQNWG PYDRDSWNPV YGNQLFMKTR    200
NGSMKAADNF LDPNKASSLL SSGFSPDFAT VITMDRKASK QQTNIDVIYE    250
RVRDDYQLHW TSTNWKGTNT KDKWTDRSSE RYKIDWEKEE MTN           293

SEQ ID NO: 18 (H35G+E111N+H144A+K147N)
ADSDINIKTG TTDIGSNTTV KTGDLVTYDK ENGMGKKVFY SFIDDKNHNK    50
KLLVIRTKGT IAGQYRVYSE EGANKSGLAW PSAFKVQLQL PDNEVAQISD    100
YYPRNSIDTK NYMSTLTYGF NGNVTGDDTG KIGGLIGANV SIGATLNYVQ    150
PDFKTILESP TDKKVGWKVI FNNMVNQNWG PYDRDSWNPV YGNQLFMKTR    200
NGSMKAADNF LDPNKASSLL SSGFSPDFAT VITMDRKASK QQTNIDVIYE    250
RVRDDYQLHW TSTNWKGTNT KDKWTDRSSE RYKIDWEKEE MTN           293

SEQ ID NO: 19 (H35G+E111N+M113A+126 131G+H144A+K147N)
ADSDINIKTG TTDIGSNTTV KTGDLVTYDK ENGMGKKVFY SFIDDKNHNK    50
KLLVIRTKGT IAGQYRVYSE EGANKSGLAW PSAFKVQLQL PDNEVAQISD    100
YYPRNSIDTK NYASTLTYGF NGNVTGGGGG GIGGLIGANV SIGATLNYVQ    150
PDFKTILESP TDKKVGWKVI FNNMVNQNWG PYDRDSWNPV YGNQLFMKTR    200
NGSMKAADNF LDPNKASSLL SSGFSPDFAT VITMDRKASK QQTNIDVIYE    250
RVRDDYQLHW TSTNWKGTNT KDKWTDRSSE RYKIDWEKEE MTN           293

SEQ ID NO: 20 (E111N+M113A+126 131G+K147N)
ADSDINIKTG TTDIGSNTTV KTGDLVTYDK ENGMHKKVFY SFIDDKNHNK    50
KLLVIRTKGT IAGQYRVYSE EGANKSGLAW PSAFKVQLQL PDNEVAQISD    100
YYPRNSIDTK NYASTLTYGF NGNVTGGGGG GIGGLIGANV SIGATLNYVQ    150
PDFKTILESP TDKKVGWKVI FNNMVNQNWG PYDRDSWNPV YGNQLFMKTR    200
NGSMKAADNF LDPNKASSLL SSGFSPDFAT VITMDRKASK QQTNIDVIYE    250
RVRDDYQLHW TSTNWKGTNT KDKWTDRSSE RYKIDWEKEE MTN           293

SEQ ID NO: 21 (linker-SpyTag protein, with linker underlined
and SpyTag in bold)
GGSSGGSSGGAHIVMVDAYKPTK SEQ ID NO: 22 (E111S M113S T145S K147S L135I)
ADSDINIKTG TTDIGSNTTV KTGDLVTYDK ENGMHKKVFY SFIDDKNHNK    50
KLLVIRTKGT IAGQYRVYSE EGANKSGLAW PSAFKVQLQL PDNEVAQISD    100
YYPRNSIDTK SYSSTLTYGF NGNVTGDDTG KIGGIIGANV SIGASLSYVQ    150
PDFKTILESP TDKKVGWKVI FNNMVNQNWG PYDRDSWNPV YGNQLFMKTR    200
NGSMKAADNF LDPNKASSLL SSGFSPDFAT VITMDRKASK QQTNIDVIYE    250
RVRDDYQLHW TSTNWKGTNT KDKWTDRSSE RYKIDWEKEE MTN           293
```

CITATION LIST

Patent Literature

[1] PCT/US2013/026514 (published as WO2013/123450) entitled "Methods for Creating Bilayers for Use with Nanopore Sensors"
[2] PCT/US2013/068967 (published as WO 2014/074727) entitled "Nucleic Acid Sequencing Using Tags"
[3] PCT/US14/61853 filed 23 Oct. 2014 entitled "Methods for Forming Lipid Bilayers on Biochips"

Non-Patent Literature

[4] Aksimentiev and Schulten, *Imaging a-Hemolysin with Molecular Dynamics: Ionic Conductance, Osmotic Permeability, and the Electrostatic Potential Map*, Biophysical Journal (2005) 88: 3745-3761.
[5] Butler et al., *Single-molecule DNA detection with an engineered MspA protein nanopore*, PNAS (2008) 105 (52): 20647-20652.
[6] Korchev et al., *Low Conductance States of a Single Ion Channel are not 'Closed'*, J. Membrane Biol. (1995) 147:233-239.
[7] Krasilnikov and Sabirov, *Ion Transport Through Channels Formed in Lipid Bilayers by Staphylococcus aureus Alpha-Toxin*, Gen. Physiol. Biophys. (1989) 8:213-222.
[8] Nakane et al., *A Nanosensor for Transmembrane Capture and Identification of Single Nucleic Acid Molecules*, Biophys. J. (2004) 87:615-621.
[9] Rhee and Burns, *Nanopore sequencing technology: nanopore preparations*, TRENDS in Biotech. (2007) 25(4):174-181.
Song et al., *Structure of Staphylococcal α-Hemolysin, a Heptameric Transmembrane Pore*, Science (1996) 274: 1859-1866.
Kasianowicz et al., *Nanometer-scale pores: potential applications for analyte detection and DNA characterization*, Proc. Natl. Acad. Sci. USA (1996) 93:13770-13773.
Akeson et al., *Microsecond timescale discrimination among polycytidylic acid, polyadenylic acid, and polyuridylic acid as homopolymers or as segments within single RNA molecules*, Biophys. J. (1999) 77:3227-3233.
Meller et al., *Voltage-driven DNA translocations through a nanopore*, Phys. Rev. Lett., 86 (2001), pp. 3435-3438.
Howorka et al., *Sequence-specific detection of individual DNA strands using engineered nanopores*, Nat. Biotechnol., 19 (2001a), pp. 636-639.
Howorka et al., *Kinetics of duplex formation for individual DNA strands within a single protein nanopore*, Proc. Natl. Acad. Sci. USA, 98 (2001b), pp. 12996-13001.
Movileanu et al., *Detecting protein analytes that modulate transmembrane movement of a polymer chain within a single protein pore*, Nat. Biotechnol., 18 (2000), pp. 1091-1095.

The entirety of each patent, patent application, publication, document, GENBANK sequence, website and other published material referenced herein hereby is incorporated by reference, including all tables, drawings, and figures. All patents and publications are herein incorporated by reference to the same extent as if each was specifically and individually indicated to be incorporated by reference. Citation of the above patents, patent applications, publications and documents is not an admission that any of the foregoing is pertinent prior art, nor does it constitute any admission as to the contents or date of these publications or documents. All patents and publications mentioned herein are indicative of the skill levels of those of ordinary skill in the art to which the invention pertains.

What is claimed is:

1. An isolated polypeptide comprising an amino acid sequence having at least 85% sequence identity to SEQ ID NO: 20, wherein the amino acid sequence comprises (a) an asparagine at a position corresponding to position 111 of SEQ ID NO: 20, (b) an alanine at a position corresponding to position 113 of SEQ ID NO: 20, (c) a glycine at positions corresponding to each of positions 35 and 126-131 of SEQ ID NO: 20, (d) an asparagine residue at a position corresponding to position 147 of SEQ ID NO: 20, and (e) an alanine at a position corresponding to position 144 of SEQ ID NO: 20.

2. The isolated peptide of claim 1, wherein the peptide further comprises a lysine at a position corresponding to position 149 of SEQ ID NO: 20.

3. The isolated peptide of claim 1, wherein the isolated peptide further comprises an attachment linker.

4. The isolated peptide of claim 3, wherein the attachment linker comprises an amino acid sequences corresponding to amino acid residues 1-10 of SEQ ID NO: 21.

5. The isolated peptide of claim 3, wherein the attachment linker is joined to a SpyTag or SpyCatcher amino acid sequence.

6. The isolated peptide of claim 5, wherein the attachment linker is joined to a SpyTag amino acid sequence, the joined attachment linker and SpyTag sequence comprising an amino acid sequence as set forth as SEQ ID NO: 21.

7. The isolated peptide of claim 5, wherein the SpyTag or SpyCatcher amino acid sequence is bound to a polymerase.

8. A heptameric nanopore assembly, the assembly comprising seven monomer units, wherein at least six of the monomer units are polypeptides according to claim 1.

9. The heptameric nanopore assembly of claim 8, wherein each of the at least six monomer units further comprises a lysine at a position corresponding to position 149 of SEQ ID NO: 20.

10. The heptameric nanopore assembly of claim 8, wherein at least 1 of the monomer units comprises an amino acid sequence that is bound to a DNA polymerase or that is configured to bind a DNA polymerase.

11. The heptameric nanopore assembly of claim 10, wherein the at least 1 monomer unit comprises an attachment linker.

12. The heptameric alpha-hemolysin nanopore assembly of claim 11, wherein the attachment linker comprises an amino acid sequences corresponding to residues 1-10 of SEQ ID NO: 21.

13. The heptameric alpha-hemolysin nanopore assembly of claim 11, wherein the attachment linker is joined to a SpyTag or SpyCatcher amino acid sequence.

14. The heptameric alpha-hemolysin nanopore assembly of claim 13, wherein the attachment linker is joined to s SpyTag amino acid sequence, the joined attachment linker and SpyTag sequence comprising an amino acid sequence as set forth as SEQ ID NO: 21.

15. The heptameric alpha-hemolysin nanopore assembly of claim 13, wherein the SpyTag or SpyCatcher amino acid sequence is bound to a polymerase.

16. The heptameric alpha-hemolysin nanopore assembly of claim 8, wherein the heptameric alpha-hemolysin nanopore assembly is disposed within a membrane of a sequencing chip.

17. The heptameric alpha-hemolysin nanopore assembly of claim 16, wherein membrane comprising the heptameric alpha-hemolysin nanopore assembly is disposed in proximity to a sensing electrode.

18. The heptameric alpha-hemolysin nanopore assembly of claim 16, wherein each of the at least six monomer units further comprises a lysine at a position corresponding to position 149 of SEQ ID NO: 20.

* * * * *

SEQUENCE LISTING

```
<160> NUMBER OF SEQ ID NOS: 22

<210> SEQ ID NO 1
<211> LENGTH: 1023
<212> TYPE: DNA
<213> ORGANISM: Staphylococcus aureus

<400> SEQUENCE: 1
atggcagatc tcgatcccgc gaaattaata cgactcacta tagggaggcc acaacggttt      60
ccctctagaa ataattttgt ttaactttaa gaaggagata tacaaatgga ttcagatatt     120
aatattaaaa caggtacaac agatattggt tcaaatacaa cagtaaaaac tggtgattta     180
gtaacttatg ataagaaaa tggtatgcat aaaaaagtat tttattcttt tattgatgat     240
aaaaatcata ataaaaaatt gttagttatt cgtacaaaag gtactattgc aggtcaatat     300
agagtatata gtgaagaagg tgctaataaa agtggtttag catggccatc tgcttttaaa     360
gttcaattac aattacctga taatgaagta gcacaaattt cagattatta tccacgtaat     420
agtattgata caaagaata tatgtcaaca ttaacttatg gttttaatgg taatgtaaca     480
ggtgatgata ctggtaaaat tggtggttta attggtgcta atgtttcaat tggtcataca     540
ttaaaatatg tacaaccaga tttaaaaca attttagaaa gtcctactga taaaaagtt     600 ggttggaaag taatttttaa taatatggtt aatcaaaatt ggggtcctta tgatcgtgat     660
agttggaatc ctgtatatgg taatcaatta tttatgaaaa caagaaatgg ttctatgaaa     720
```

```
gcagctgata atttcttaga tccaaataaa gcatcaagtt tattatcttc aggtttttct      780
cctgattttg caacagttat tactatggat agaaaagcat caaaacaaca aacaaatatt      840
gatgttattt atgaacgtgt aagagatgat tatcaattac attggacatc aactaattgg      900
aaaggtacaa atactaaaga taaatggaca gatagaagtt cagaaagata taaaattgat      960
tgggaaaaag aagaaatgac aaatggtctc agcgcttgga gccacccgca gttcgaaaaa     1020
taa                                                                   1023
```

<210> SEQ ID NO 2
<211> LENGTH: 306
<212> TYPE: PRT
<213> ORGANISM: Artificial Sequence
<220> FEATURE:
<223> OTHER INFORMATION: wild-type alpha-hemolysin with purification tag

<400> SEQUENCE: 2

```
Met Ala Asp Ser Asp Ile Asn Ile Lys Thr Gly Thr Thr Asp Ile Gly
1               5                   10                  15

Ser Asn Thr Thr Val Lys Thr Gly Asp Leu Val Thr Tyr Asp Lys Glu
            20                  25                  30

Asn Gly Met His Lys Lys Val Phe Tyr Ser Phe Ile Asp Asp Lys Asn
        35                  40                  45

His Asn Lys Lys Leu Leu Val Ile Arg Thr Lys Gly Thr Ile Ala Gly
    50                  55                  60

Gln Tyr Arg Val Tyr Ser Glu Glu Gly Ala Asn Lys Ser Gly Leu Ala
65                  70                  75                  80

Trp Pro Ser Ala Phe Lys Val Gln Leu Gln Leu Pro Asp Asn Glu Val
                85                  90                  95

Ala Gln Ile Ser Asp Tyr Tyr Pro Arg Asn Ser Ile Asp Thr Lys Glu
            100                 105                 110

Tyr Met Ser Thr Leu Thr Tyr Gly Phe Asn Gly Asn Val Thr Gly Asp
        115                 120                 125

Asp Thr Gly Lys Ile Gly Gly Leu Ile Gly Ala Asn Val Ser Ile Gly
    130                 135                 140

His Thr Leu Lys Tyr Val Gln Pro Asp Phe Lys Thr Ile Leu Glu Ser
145                 150                 155                 160

Pro Thr Asp Lys Lys Val Gly Trp Lys Val Ile Phe Asn Asn Met Val
                165                 170                 175

Asn Gln Asn Trp Gly Pro Tyr Asp Arg Asp Ser Trp Asn Pro Val Tyr
            180                 185                 190

Gly Asn Gln Leu Phe Met Lys Thr Arg Asn Gly Ser Met Lys Ala Ala
        195                 200                 205

Asp Asn Phe Leu Asp Pro Asn Lys Ala Ser Ser Leu Leu Ser Ser Gly
    210                 215                 220

Phe Ser Pro Asp Phe Ala Thr Val Ile Thr Met Asp Arg Lys Ala Ser
225                 230                 235                 240

Lys Gln Gln Thr Asn Ile Asp Val Ile Tyr Glu Arg Val Arg Asp Asp
                245                 250                 255

Tyr Gln Leu His Trp Thr Ser Thr Asn Trp Lys Gly Thr Asn Thr Lys
            260                 265                 270

Asp Lys Trp Thr Asp Arg Ser Ser Glu Arg Tyr Lys Ile Asp Trp Glu
        275                 280                 285

Lys Glu Glu Met Thr Asn Gly Leu Ser Ala Trp Ser His Pro Gln Phe
    290                 295                 300
```

Glu Lys
305

<210> SEQ ID NO 3
<211> LENGTH: 305
<212> TYPE: PRT
<213> ORGANISM: Artificial Sequence
<220> FEATURE:
<223> OTHER INFORMATION: mature wild-type alpha-hemolysin with
      purification tag

<400> SEQUENCE: 3

Ala Asp Ser Asp Ile Asn Ile Lys Thr Gly Thr Thr Asp Ile Gly Ser
1               5                   10                  15

Asn Thr Thr Val Lys Thr Gly Asp Leu Val Thr Tyr Asp Lys Glu Asn
            20                  25                  30

Gly Met His Lys Lys Val Phe Tyr Ser Phe Ile Asp Asp Lys Asn His
        35                  40                  45

Asn Lys Lys Leu Leu Val Ile Arg Thr Lys Gly Thr Ile Ala Gly Gln
    50                  55                  60

Tyr Arg Val Tyr Ser Glu Glu Gly Ala Asn Lys Ser Gly Leu Ala Trp
65                  70                  75                  80

Pro Ser Ala Phe Lys Val Gln Leu Gln Leu Pro Asp Asn Glu Val Ala
                85                  90                  95

Gln Ile Ser Asp Tyr Tyr Pro Arg Asn Ser Ile Asp Thr Lys Glu Tyr
            100                 105                 110

Met Ser Thr Leu Thr Tyr Gly Phe Asn Gly Asn Val Thr Gly Asp Asp
        115                 120                 125

Thr Gly Lys Ile Gly Gly Leu Ile Gly Ala Asn Val Ser Ile Gly His
    130                 135                 140

Thr Leu Lys Tyr Val Gln Pro Asp Phe Lys Thr Ile Leu Glu Ser Pro
145                 150                 155                 160

Thr Asp Lys Lys Val Gly Trp Lys Val Ile Phe Asn Asn Met Val Asn
                165                 170                 175

Gln Asn Trp Gly Pro Tyr Asp Arg Asp Ser Trp Asn Pro Val Tyr Gly
            180                 185                 190

Asn Gln Leu Phe Met Lys Thr Arg Asn Gly Ser Met Lys Ala Ala Asp
        195                 200                 205

Asn Phe Leu Asp Pro Asn Lys Ala Ser Ser Leu Leu Ser Ser Gly Phe
    210                 215                 220

Ser Pro Asp Phe Ala Thr Val Ile Thr Met Asp Arg Lys Ala Ser Lys
225                 230                 235                 240

Gln Gln Thr Asn Ile Asp Val Ile Tyr Glu Arg Val Arg Asp Asp Tyr
                245                 250                 255

Gln Leu His Trp Thr Ser Thr Asn Trp Lys Gly Thr Asn Thr Lys Asp
            260                 265                 270

Lys Trp Thr Asp Arg Ser Ser Glu Arg Tyr Lys Ile Asp Trp Glu Lys
        275                 280                 285

Glu Glu Met Thr Asn Gly Leu Ser Ala Trp Ser His Pro Gln Phe Glu
    290                 295                 300

Lys
305

<210> SEQ ID NO 4
<211> LENGTH: 293
<212> TYPE: PRT

<213> ORGANISM: Artificial Sequence
<220> FEATURE:
<223> OTHER INFORMATION: H35G+V149K+H144A alpha-hemolysin

<400> SEQUENCE: 4

```
Ala Asp Ser Asp Ile Asn Ile Lys Thr Gly Thr Thr Asp Ile Gly Ser
1               5                   10                  15

Asn Thr Thr Val Lys Thr Gly Asp Leu Val Thr Tyr Asp Lys Glu Asn
            20                  25                  30

Gly Met Gly Lys Lys Val Phe Tyr Ser Phe Ile Asp Asp Lys Asn His
        35                  40                  45

Asn Lys Lys Leu Leu Val Ile Arg Thr Lys Gly Thr Ile Ala Gly Gln
50                  55                  60

Tyr Arg Val Tyr Ser Glu Glu Gly Ala Asn Lys Ser Gly Leu Ala Trp
65                  70                  75                  80

Pro Ser Ala Phe Lys Val Gln Leu Gln Leu Pro Asp Asn Glu Val Ala
                85                  90                  95

Gln Ile Ser Asp Tyr Tyr Pro Arg Asn Ser Ile Asp Thr Lys Glu Tyr
            100                 105                 110

Met Ser Thr Leu Thr Tyr Gly Phe Asn Gly Asn Val Thr Gly Asp Asp
        115                 120                 125

Thr Gly Lys Ile Gly Gly Leu Ile Gly Ala Asn Val Ser Ile Gly Ala
130                 135                 140

Thr Leu Lys Tyr Lys Gln Pro Asp Phe Lys Thr Ile Leu Glu Ser Pro
145                 150                 155                 160

Thr Asp Lys Lys Val Gly Trp Lys Val Ile Phe Asn Asn Met Val Asn
                165                 170                 175

Gln Asn Trp Gly Pro Tyr Asp Arg Asp Ser Trp Asn Pro Val Tyr Gly
            180                 185                 190

Asn Gln Leu Phe Met Lys Thr Arg Asn Gly Ser Met Lys Ala Ala Asp
        195                 200                 205

Asn Phe Leu Asp Pro Asn Lys Ala Ser Ser Leu Leu Ser Ser Gly Phe
210                 215                 220

Ser Pro Asp Phe Ala Thr Val Ile Thr Met Asp Arg Lys Ala Ser Lys
225                 230                 235                 240

Gln Gln Thr Asn Ile Asp Val Ile Tyr Glu Arg Val Arg Asp Asp Tyr
                245                 250                 255

Gln Leu His Trp Thr Ser Thr Asn Trp Lys Gly Thr Asn Thr Lys Asp
            260                 265                 270

Lys Trp Thr Asp Arg Ser Ser Glu Arg Tyr Lys Ile Asp Trp Glu Lys
        275                 280                 285

Glu Glu Met Thr Asn
    290
```

<210> SEQ ID NO 5
<211> LENGTH: 293
<212> TYPE: PRT
<213> ORGANISM: Artificial Sequence
<220> FEATURE:
<223> OTHER INFORMATION: H35G+H144A+V149K+E287R alpha-hemolysin

<400> SEQUENCE: 5

```
Ala Asp Ser Asp Ile Asn Ile Lys Thr Gly Thr Thr Asp Ile Gly Ser
1               5                   10                  15

Asn Thr Thr Val Lys Thr Gly Asp Leu Val Thr Tyr Asp Lys Glu Asn
            20                  25                  30
```

```
Gly Met Gly Lys Lys Val Phe Tyr Ser Phe Ile Asp Lys Asn His
            35                  40                  45

Asn Lys Lys Leu Leu Val Ile Arg Thr Lys Gly Thr Ile Ala Gly Gln
 50                  55                  60

Tyr Arg Val Tyr Ser Glu Glu Gly Ala Asn Lys Ser Gly Leu Ala Trp
 65                  70                  75                  80

Pro Ser Ala Phe Lys Val Gln Leu Gln Leu Pro Asp Asn Glu Val Ala
                 85                  90                  95

Gln Ile Ser Asp Tyr Tyr Pro Arg Asn Ser Ile Asp Thr Lys Glu Tyr
            100                 105                 110

Met Ser Thr Leu Thr Tyr Gly Phe Asn Gly Asn Val Thr Gly Asp Asp
        115                 120                 125

Thr Gly Lys Ile Gly Gly Leu Ile Gly Ala Asn Val Ser Ile Gly Ala
130                 135                 140

Thr Leu Lys Tyr Lys Gln Pro Asp Phe Lys Thr Ile Leu Glu Ser Pro
145                 150                 155                 160

Thr Asp Lys Lys Val Gly Trp Lys Val Ile Phe Asn Asn Met Val Asn
                165                 170                 175

Gln Asn Trp Gly Pro Tyr Asp Arg Asp Ser Trp Asn Pro Val Tyr Gly
            180                 185                 190

Asn Gln Leu Phe Met Lys Thr Arg Asn Gly Ser Met Lys Ala Ala Asp
        195                 200                 205

Asn Phe Leu Asp Pro Asn Lys Ala Ser Ser Leu Leu Ser Ser Gly Phe
210                 215                 220

Ser Pro Asp Phe Ala Thr Val Ile Thr Met Asp Arg Lys Ala Ser Lys
225                 230                 235                 240

Gln Gln Thr Asn Ile Asp Val Ile Tyr Glu Arg Val Arg Asp Asp Tyr
                245                 250                 255

Gln Leu His Trp Thr Ser Thr Asn Trp Lys Gly Thr Asn Thr Lys Asp
            260                 265                 270

Lys Trp Thr Asp Arg Ser Ser Glu Arg Tyr Lys Ile Asp Trp Arg Lys
        275                 280                 285

Glu Glu Met Thr Asn
    290
```

<210> SEQ ID NO 6
<211> LENGTH: 293
<212> TYPE: PRT
<213> ORGANISM: Artificial Sequence
<220> FEATURE:
<223> OTHER INFORMATION: V149K+E287R alpha-hemolysin

<400> SEQUENCE: 6

```
Ala Asp Ser Asp Ile Asn Ile Lys Thr Gly Thr Thr Asp Ile Gly Ser
 1               5                  10                  15

Asn Thr Thr Val Lys Thr Gly Asp Leu Val Thr Tyr Asp Lys Glu Asn
                20                  25                  30

Gly Met Gly Lys Lys Val Phe Tyr Ser Phe Ile Asp Lys Asn His
            35                  40                  45

Asn Lys Lys Leu Leu Val Ile Arg Thr Lys Gly Thr Ile Ala Gly Gln
 50                  55                  60

Tyr Arg Val Tyr Ser Glu Glu Gly Ala Asn Lys Ser Gly Leu Ala Trp
 65                  70                  75                  80

Pro Ser Ala Phe Lys Val Gln Leu Gln Leu Pro Asp Asn Glu Val Ala
                 85                  90                  95
```

```
Gln Ile Ser Asp Tyr Tyr Pro Arg Asn Ser Ile Asp Thr Lys Glu Tyr
            100                 105                 110

Met Ser Thr Leu Thr Tyr Gly Phe Asn Gly Asn Val Thr Gly Asp Asp
        115                 120                 125

Thr Gly Lys Ile Gly Gly Leu Ile Gly Ala Asn Val Ser Ile Gly His
    130                 135                 140

Thr Leu Lys Tyr Lys Gln Pro Asp Phe Lys Thr Ile Leu Glu Ser Pro
145                 150                 155                 160

Thr Asp Lys Lys Val Gly Trp Lys Val Ile Phe Asn Asn Met Val Asn
                165                 170                 175

Gln Asn Trp Gly Pro Tyr Asp Arg Asp Ser Trp Asn Pro Val Tyr Gly
            180                 185                 190

Asn Gln Leu Phe Met Lys Thr Arg Asn Gly Ser Met Lys Ala Ala Asp
        195                 200                 205

Asn Phe Leu Asp Pro Asn Lys Ala Ser Ser Leu Leu Ser Ser Gly Phe
    210                 215                 220

Ser Pro Asp Phe Ala Thr Val Ile Thr Met Asp Arg Lys Ala Ser Lys
225                 230                 235                 240

Gln Gln Thr Asn Ile Asp Val Ile Tyr Glu Arg Val Arg Asp Asp Tyr
                245                 250                 255

Gln Leu His Trp Thr Ser Thr Asn Trp Lys Gly Thr Asn Thr Lys Asp
            260                 265                 270

Lys Trp Thr Asp Arg Ser Ser Glu Arg Tyr Lys Ile Asp Trp Arg Lys
        275                 280                 285

Glu Glu Met Thr Asn
    290

<210> SEQ ID NO 7
<211> LENGTH: 293
<212> TYPE: PRT
<213> ORGANISM: Artificial Sequence
<220> FEATURE:
<223> OTHER INFORMATION: T109K+H35G alpha-hemolysin

<400> SEQUENCE: 7

Ala Asp Ser Asp Ile Asn Ile Lys Thr Gly Thr Thr Asp Ile Gly Ser
1               5                   10                  15

Asn Thr Thr Val Lys Thr Gly Asp Leu Val Thr Tyr Asp L

```
Thr Asp Lys Lys Val Gly Trp Lys Val Ile Phe Asn Asn Met Val Asn
            165                 170                 175

Gln Asn Trp Gly Pro Tyr Asp Arg Asp Ser Trp Asn Pro Val Tyr Gly
        180                 185                 190

Asn Gln Leu Phe Met Lys Thr Arg Asn Gly Ser Met Lys Ala Ala Asp
        195                 200                 205

Asn Phe Leu Asp Pro Asn Lys Ala Ser Ser Leu Leu Ser Ser Gly Phe
        210                 215                 220

Ser Pro Asp Phe Ala Thr Val Ile Thr Met Asp Arg Lys Ala Ser Lys
225                 230                 235                 240

Gln Gln Thr Asn Ile Asp Val Ile Tyr Glu Arg Val Arg Asp Asp Tyr
            245                 250                 255

Gln Leu His Trp Thr Ser Thr Asn Trp Lys Gly Thr Asn Thr Lys Asp
            260                 265                 270

Lys Trp Thr Asp Arg Ser Ser Glu Arg Tyr Lys Ile Asp Trp Glu Lys
            275                 280                 285

Glu Glu Met Thr Asn
            290

<210> SEQ ID NO 8
<211> LENGTH: 293
<212> TYPE: PRT
<213> ORGANISM: Artificial Sequence
<220> FEATURE:
<223> OTHER INFORMATION: P151K+H35G alpha-hemolysin

<400> SEQUENCE: 8

Ala Asp Ser Asp Ile Asn Ile Lys Thr Gly Thr Thr Asp Ile Gly Ser
1               5                   10                  15

Asn Thr Thr Val Lys Thr Gly Asp Leu Val Thr Tyr Asp Lys Glu Asn
            20                  25                  30

Gly Met Gly Lys Lys Val Phe Tyr Ser Phe Ile Asp Asp Lys Asn His
        35                  40                  45

Asn Lys Lys Leu Leu Val Ile Arg Thr Lys Gly Thr Ile Ala Gly Gln
    50                  55                  60

Tyr Arg Val Tyr Ser Glu Glu Gly Ala Asn Lys Ser Gly Leu Ala Trp
65                  70                  75                  80

Pro Ser Ala Phe Lys Val Gln Leu Gln Leu Pro Asp Asn Glu Val Ala
                85                  90                  95

Gln Ile Ser Asp Tyr Tyr Pro Arg Asn Ser Ile Asp Thr Lys Glu Tyr
            100                 105                 110

Met Ser Thr Leu Thr Tyr Gly Phe Asn Gly Asn Val Thr Gly Asp Asp
        115                 120                 125

Thr Gly Lys Ile Gly Gly Leu Ile Gly Ala Asn Val Ser Ile Gly Ala
    130                 135                 140

Thr Leu Lys Tyr Val Gln Lys Asp Phe Lys Thr Ile Leu Glu Ser Pro
145                 150                 155                 160

Thr Asp Lys Lys Val Gly Trp Lys Val Ile Phe Asn Asn Met Val Asn
            165                 170                 175

Gln Asn Trp Gly Pro Tyr Asp Arg Asp Ser Trp Asn Pro Val Tyr Gly
        180                 185                 190

Asn Gln Leu Phe Met Lys Thr Arg Asn Gly Ser Met Lys Ala Ala Asp
        195                 200                 205

Asn Phe Leu Asp Pro Asn Lys Ala Ser Ser Leu Leu Ser Ser Gly Phe
        210                 215                 220
```

```
Ser Pro Asp Phe Ala Thr Val Ile Thr Met Asp Arg Lys Ala Ser Lys
225                 230                 235                 240

Gln Gln Thr Asn Ile Asp Val Ile Tyr Glu Arg Val Arg Asp Asp Tyr
            245                 250                 255

Gln Leu His Trp Thr Ser Thr Asn Trp Lys Gly Thr Asn Thr Lys Asp
        260                 265                 270

Lys Trp Thr Asp Arg Ser Ser Glu Arg Tyr Lys Ile Asp Trp Glu Lys
    275                 280                 285

Glu Glu Met Thr Asn
    290
```

<210> SEQ ID NO 9
<211> LENGTH: 293
<212> TYPE: PRT
<213> ORGANISM: Artificial Sequence
<220> FEATURE:
<223> OTHER INFORMATION: V149K+P151K+H35G alpha-hemolysin

<400> SEQUENCE: 9

```
Ala Asp Ser Asp Ile Asn Ile Lys Thr Gly Thr Thr Asp Ile Gly Ser
1               5                   10                  15

Asn Thr Thr Val Lys Thr Gly Asp Leu Val Thr Tyr Asp Lys Glu Asn
            20                  25                  30

Gly Met Gly Lys Lys Val Phe Tyr Ser Phe Ile Asp Asp Lys Asn His
        35                  40                  45

Asn Lys Lys Leu Leu Val Ile Arg Thr Lys Gly Thr Ile Ala Gly Gln
    50                  55                  60

Tyr Arg Val Tyr Ser Glu Glu Gly Ala Asn Lys Ser Gly Leu Ala Trp
65                  70                  75                  80

Pro Ser Ala Phe Lys Val Gln Leu Gln Leu Pro Asp Asn Glu Val Ala
                85                  90                  95

Gln Ile Ser Asp Tyr Tyr Pro Arg Asn Ser Ile Asp Thr Lys Glu Tyr
            100                 105                 110

Met Ser Thr Leu Thr Tyr Gly Phe Asn Gly Asn Val Thr Gly Asp Asp
        115                 120                 125

Thr Gly Lys Ile Gly Gly Leu Ile Gly Ala Asn Val Ser Ile Gly Ala
    130                 135                 140

Thr Leu Lys Tyr Lys Gln Lys Asp Phe Lys Thr Ile Leu Glu Ser Pro
145                 150                 155                 160

Thr Asp Lys Lys Val Gly Trp Lys Val Ile Phe Asn Asn Met Val Asn
                165                 170                 175

Gln Asn Trp Gly Pro Tyr Asp Arg Asp Ser Trp Asn Pro Val Tyr Gly
            180                 185                 190

Asn Gln Leu Phe Met Lys Thr Arg Asn Gly Ser Met Lys Ala Ala Asp
        195                 200                 205

Asn Phe Leu Asp Pro Asn Lys Ala Ser Ser Leu Leu Ser Ser Gly Phe
    210                 215                 220

Ser Pro Asp Phe Ala Thr Val Ile Thr Met Asp Arg Lys Ala Ser Lys
225                 230                 235                 240

Gln Gln Thr Asn Ile Asp Val Ile Tyr Glu Arg Val Arg Asp Asp Tyr
                245                 250                 255

Gln Leu His Trp Thr Ser Thr Asn Trp Lys Gly Thr Asn Thr Lys Asp
            260                 265                 270

Lys Trp Thr Asp Arg Ser Ser Glu Arg Tyr Lys Ile Asp Trp Glu Lys
        275                 280                 285
```

```
<210> SEQ ID NO 10
<211> LENGTH: 293
<212> TYPE: PRT
<213> ORGANISM: Artificial Sequence
<220> FEATURE:
<223> OTHER INFORMATION: T109K+V149K+H35G

<400> SEQUENCE: 10
```

Ala Asp Ser Asp Ile Asn Ile Lys Thr Gly Thr Thr Asp Ile Gly Ser
1               5                   10                  15

Asn Thr Thr Val Lys Thr Gly Asp Leu Val Thr Tyr Asp Lys Glu Asn
            20                  25                  30

Gly Met Gly Lys Lys Val Phe Tyr Ser Phe Ile Asp Asp Lys Asn His
        35                  40                  45

Asn Lys Lys Leu Leu Val Ile Arg Thr Lys Gly Thr Ile Ala Gly Gln
50                  55                  60

Tyr Arg Val Tyr Ser Glu Glu Gly Ala Asn Lys Ser Gly Leu Ala Trp
65                  70                  75                  80

Pro Ser Ala Phe Lys Val Gln Leu Gln Leu Pro Asp Asn Glu Val Ala
                85                  90                  95

Gln Ile Ser Asp Tyr Tyr Pro Arg Asn Ser Ile Asp Lys Lys Glu Tyr
            100                 105                 110

Met Ser Thr Leu Thr Tyr Gly Phe Asn Gly Asn Val Thr Gly Asp Asp
        115                 120                 125

Thr Gly Lys Ile Gly Gly Leu Ile Gly Ala Asn Val Ser Ile Gly Ala
130                 135                 140

Thr Leu Lys Tyr Lys Gln Pro Asp Phe Lys Thr Ile Leu Glu Ser Pro
145                 150                 155                 160

Thr Asp Lys Lys Val Gly Trp Lys Val Ile Phe Asn Asn Met Val Asn
                165                 170                 175

Gln Asn Trp Gly Pro Tyr Asp Arg Asp Ser Trp Asn Pro Val Tyr Gly
            180                 185                 190

Asn Gln Leu Phe Met Lys Thr Arg Asn Gly Ser Met Lys Ala Ala Asp
        195                 200                 205

Asn Phe Leu Asp Pro Asn Lys Ala Ser Ser Leu Leu Ser Ser Gly Phe
210                 215                 220

Ser Pro Asp Phe Ala Thr Val Ile Thr Met Asp Arg Lys Ala Ser Lys
225                 230                 235                 240

Gln Gln Thr Asn Ile Asp Val Ile Tyr Glu Arg Val Arg Asp Asp Tyr
                245                 250                 255

Gln Leu His Trp Thr Ser Thr Asn Trp Lys Gly Thr Asn Thr Lys Asp
            260                 265                 270

Lys Trp Thr Asp Arg Ser Ser Glu Arg Tyr Lys Ile Asp Trp Glu Lys
        275                 280                 285

Glu Glu Met Thr Asn
    290

```
<210> SEQ ID NO 11
<211> LENGTH: 293
<212> TYPE: PRT
<213> ORGANISM: Artificial Sequence
<220> FEATURE:
<223> OTHER INFORMATION: V149K+K147N+E111N+127 131G+M113A+H35G
      alpha-hemolysin
```

<400> SEQUENCE: 11

Ala Asp Ser Asp Ile Asn Ile Lys Thr Gly Thr Thr Asp Ile Gly Ser
1               5                   10                  15

Asn Thr Thr Val Lys Thr Gly Asp Leu Val Thr Tyr Asp Lys Glu Asn
                20                  25                  30

Gly Met Gly Lys Lys Val Phe Tyr Ser Phe Ile Asp Asp Lys Asn His
            35                  40                  45

Asn Lys Lys Leu Leu Val Ile Arg Thr Lys Gly Thr Ile Ala Gly Gln
        50                  55                  60

Tyr Arg Val Tyr Ser Glu Glu Gly Ala Asn Lys Ser Gly Leu Ala Trp
65                  70                  75                  80

Pro Ser Ala Phe Lys Val Gln Leu Gln Leu Pro Asp Asn Glu Val Ala
                85                  90                  95

Gln Ile Ser Asp Tyr Tyr Pro Arg Asn Ser Ile Asp Thr Lys Asn Tyr
            100                 105                 110

Ala Ser Thr Leu Thr Tyr Gly Phe Asn Gly Asn Val Thr Gly Gly Gly
        115                 120                 125

Gly Gly Gly Ile Gly Gly Leu Ile Gly Ala Asn Val Ser Ile Gly Ala
    130                 135                 140

Thr Leu Asn Tyr Lys Gln Pro Asp Phe Lys Thr Ile Leu Glu Ser Pro
145                 150                 155                 160

Thr Asp Lys Lys Val Gly Trp Lys Val Ile Phe Asn Asn Met Val Asn
                165                 170                 175

Gln Asn Trp Gly Pro Tyr Asp Arg Asp Ser Trp Asn Pro Val Tyr Gly
            180                 185                 190

Asn Gln Leu Phe Met Lys Thr Arg Asn Gly Ser Met Lys Ala Ala Asp
        195                 200                 205

Asn Phe Leu Asp Pro Asn Lys Ala Ser Ser Leu Leu Ser Ser Gly Phe
    210                 215                 220

Ser Pro Asp Phe Ala Thr Val Ile Thr Met Asp Arg Lys Ala Ser Lys
225                 230                 235                 240

Gln Gln Thr Asn Ile Asp Val Ile Tyr Glu Arg Val Arg Asp Asp Tyr
                245                 250                 255

Gln Leu His Trp Thr Ser Thr Asn Trp Lys Gly Thr Asn Thr Lys Asp
            260                 265                 270

Lys Trp Thr Asp Arg Ser Ser Glu Arg Tyr Lys Ile Asp Trp Glu Lys
        275                 280                 285

Glu Glu Met Thr Asn
        290

<210> SEQ ID NO 12
<211> LENGTH: 293
<212> TYPE: PRT
<213> ORGANISM: Artificial Sequence
<220> FEATURE:
<223> OTHER INFORMATION: V149K+K147N+E111N+127 131G+M113A
      alpha-hemolysin

<400> SEQUENCE: 12

Ala Asp Ser Asp Ile Asn Ile Lys Thr Gly Thr Thr Asp Ile Gly Ser
1               5                   10                  15

Asn Thr Thr Val Lys Thr Gly Asp Leu Val Thr Tyr Asp Lys Glu Asn
                20                  25                  30

Gly Met His Lys Lys Val Phe Tyr Ser Phe Ile Asp Asp Lys Asn His
            35                  40                  45

-continued

```
Asn Lys Lys Leu Leu Val Ile Arg Thr Lys Gly Thr Ile Ala Gly Gln
 50                  55                  60

Tyr Arg Val Tyr Ser Glu Glu Gly Ala Asn Lys Ser Gly Leu Ala Trp
 65                  70                  75                  80

Pro Ser Ala Phe Lys Val Gln Leu Gln Leu Pro Asp Asn Glu Val Ala
                 85                  90                  95

Gln Ile Ser Asp Tyr Tyr Pro Arg Asn Ser Ile Asp Thr Lys Asn Tyr
            100                 105                 110

Ala Ser Thr Leu Thr Tyr Gly Phe Asn Gly Asn Val Thr Gly Gly Gly
        115                 120                 125

Gly Gly Gly Ile Gly Gly Leu Ile Gly Ala Asn Val Ser Ile Gly His
130                 135                 140

Thr Leu Asn Tyr Lys Gln Pro Asp Phe Lys Thr Ile Leu Glu Ser Pro
145                 150                 155                 160

Thr Asp Lys Lys Val Gly Trp Lys Val Ile Phe Asn Asn Met Val Asn
                165                 170                 175

Gln Asn Trp Gly Pro Tyr Asp Arg Asp Ser Trp Asn Pro Val Tyr Gly
            180                 185                 190

Asn Gln Leu Phe Met Lys Thr Arg Asn Gly Ser Met Lys Ala Ala Asp
        195                 200                 205

Asn Phe Leu Asp Pro Asn Lys Ala Ser Ser Leu Leu Ser Ser Gly Phe
210                 215                 220

Ser Pro Asp Phe Ala Thr Val Ile Thr Met Asp Arg Lys Ala Ser Lys
225                 230                 235                 240

Gln Gln Thr Asn Ile Asp Val Ile Tyr Glu Arg Val Arg Asp Asp Tyr
                245                 250                 255

Gln Leu His Trp Thr Ser Thr Asn Trp Lys Gly Thr Asn Thr Lys Asp
            260                 265                 270

Lys Trp Thr Asp Arg Ser Ser Glu Arg Tyr Lys Ile Asp Trp Glu Lys
        275                 280                 285

Glu Glu Met Thr Asn
        290

<210> SEQ ID NO 13
<211> LENGTH: 293
<212> TYPE: PRT
<213> ORGANISM: Artificial Sequence
<220> FEATURE:
<223> OTHER INFORMATION: T109K+V149K+P151K+H35G alpha-hemolysin

<400> SEQUENCE: 13

Ala Asp Ser Asp Ile Asn Ile Lys Thr Gly Thr Thr Asp Ile Gly Ser
 1               5                  10                  15

Asn Thr Thr Val Lys Thr Gly Asp Leu Val Thr Tyr Asp Lys Glu Asn
                 20                  25                  30

Gly Met Gly Lys Lys Val Phe Tyr Ser Phe Ile Asp Asp Lys Asn His
             35                  40                  45

Asn Lys Lys Leu Leu Val Ile Arg Thr Lys Gly Thr Ile Ala Gly Gln
 50                  55                  60

Tyr Arg Val Tyr Ser Glu Glu Gly Ala Asn Lys Ser Gly Leu Ala Trp
 65                  70                  75                  80

Pro Ser Ala Phe Lys Val Gln Leu Gln Leu Pro Asp Asn Glu Val Ala
                 85                  90                  95

Gln Ile Ser Asp Tyr Tyr Pro Arg Asn Ser Ile Asp Lys Lys Glu Tyr
            100                 105                 110
```

```
Met Ser Thr Leu Thr Tyr Gly Phe Asn Gly Asn Val Thr Gly Asp Asp
            115                 120                 125

Thr Gly Lys Ile Gly Gly Leu Ile Gly Ala Asn Val Ser Ile Gly Ala
    130                 135                 140

Thr Leu Lys Tyr Lys Gln Lys Asp Phe Lys Thr Ile Leu Glu Ser Pro
145                 150                 155                 160

Thr Asp Lys Lys Val Gly Trp Lys Val Ile Phe Asn Asn Met Val Asn
                165                 170                 175

Gln Asn Trp Gly Pro Tyr Asp Arg Asp Ser Trp Asn Pro Val Tyr Gly
            180                 185                 190

Asn Gln Leu Phe Met Lys Thr Arg Asn Gly Ser Met Lys Ala Ala Asp
        195                 200                 205

Asn Phe Leu Asp Pro Asn Lys Ala Ser Ser Leu Leu Ser Ser Gly Phe
    210                 215                 220

Ser Pro Asp Phe Ala Thr Val Ile Thr Met Asp Arg Lys Ala Ser Lys
225                 230                 235                 240

Gln Gln Thr Asn Ile Asp Val Ile Tyr Glu Arg Val Arg Asp Asp Tyr
                245                 250                 255

Gln Leu His Trp Thr Ser Thr Asn Trp Lys Gly Thr Asn Thr Lys Asp
            260                 265                 270

Lys Trp Thr Asp Arg Ser Ser Glu Arg Tyr Lys Ile Asp Trp Glu Lys
        275                 280                 285

Glu Glu Met Thr Asn
    290

<210> SEQ ID NO 14
<211> LENGTH: 293
<212> TYPE: PRT
<213> ORGANISM: Staphylococcus aureus

<400> SEQUENCE: 14

Ala Asp Ser Asp Ile Asn Ile Lys Thr Gly Thr Thr Asp Ile Gly Ser
1               5                   10                  15

Asn Thr Thr Val Lys Thr Gly Asp Leu Val Thr Tyr Asp Lys Glu Asn
                20                  25                  30

Gly Met His Lys Lys Val Phe Tyr Ser Phe Ile Asp Asp Lys Asn His
            35                  40                  45

Asn Lys Lys Leu Leu Val Ile Arg Thr Lys Gly Thr Ile Ala Gly Gln
    50                  55                  60

Tyr Arg Val Tyr Ser Glu Glu Gly Ala Asn Lys Ser Gly Leu Ala Trp
65                  70                  75                  80

Pro Ser Ala Phe Lys Val Gln Leu Gln Leu Pro Asp Asn Glu Val Ala
                85                  90                  95

Gln Ile Ser Asp Tyr Tyr Pro Arg Asn Ser Ile Asp Thr Lys Glu Tyr
            100                 105                 110

Met Ser Thr Leu Thr Tyr Gly Phe Asn Gly Asn Val Thr Gly Asp Asp
        115                 120                 125

Thr Gly Lys Ile Gly Gly Leu Ile Gly Ala Asn Val Ser Ile Gly His
    130                 135                 140

Thr Leu Lys Tyr Val Gln Pro Asp Phe Lys Thr Ile Leu Glu Ser Pro
145                 150                 155                 160

Thr Asp Lys Lys Val Gly Trp Lys Val Ile Phe Asn Asn Met Val Asn
                165                 170                 175

Gln Asn Trp Gly Pro Tyr Asp Arg Asp Ser Trp Asn Pro Val Tyr Gly
            180                 185                 190
```

```
Asn Gln Leu Phe Met Lys Thr Arg Asn Gly Ser Met Lys Ala Ala Asp
            195                 200                 205

Asn Phe Leu Asp Pro Asn Lys Ala Ser Ser Leu Leu Ser Ser Gly Phe
        210                 215                 220

Ser Pro Asp Phe Ala Thr Val Ile Thr Met Asp Arg Lys Ala Ser Lys
225                 230                 235                 240

Gln Gln Thr Asn Ile Asp Val Ile Tyr Glu Arg Val Arg Asp Tyr
                245                 250                 255

Gln Leu His Trp Thr Ser Thr Asn Trp Lys Gly Thr Asn Thr Lys Asp
            260                 265                 270

Lys Trp Thr Asp Arg Ser Ser Glu Arg Tyr Lys Ile Asp Trp Glu Lys
        275                 280                 285

Glu Glu Met Thr Asn
    290
```

<210> SEQ ID NO 15
<211> LENGTH: 739
<212> TYPE: PRT
<213> ORGANISM: Artificial Sequence
<220> FEATURE:
<223> OTHER INFORMATION: His-tagged Clostridium phage phiCPV4 pol6

<400> SEQUENCE: 15

```
Met His His His His His His His Ser Gly Gly Ser Asp Lys His
1               5                   10                  15

Thr Gln Tyr Val Lys Glu His Ser Phe Asn Tyr Asp Glu Tyr Lys Lys
            20                  25                  30

Ala Asn Phe Asp Lys Ile Glu Cys Leu Ile Phe Asp Thr Glu Ser Cys
        35                  40                  45

Thr Asn Tyr Glu Asn Asp Asn Thr Gly Ala Arg Val Tyr Gly Trp Gly
    50                  55                  60

Leu Gly Val Thr Arg Asn His Asn Met Ile Tyr Gly Gln Asn Leu Asn
65                  70                  75                  80

Gln Phe Trp Glu Val Cys Gln Asn Ile Phe Asn Asp Trp Tyr His Asp
                85                  90                  95

Asn Lys His Thr Ile Lys Ile Thr Lys Thr Lys Lys Gly Phe Pro Lys
            100                 105                 110

Arg Lys Tyr Ile Lys Phe Pro Ile Ala Val His Asn Leu Gly Trp Asp
        115                 120                 125

Val Glu Phe Leu Lys Tyr Ser Leu Val Glu Asn Gly Phe Asn Tyr Asp
    130                 135                 140

Lys Gly Leu Leu Lys Thr Val Phe Ser Lys Gly Ala Pro Tyr Gln Thr
145                 150                 155                 160

Val Thr Asp Val Glu Glu Pro Lys Thr Phe His Ile Val Gln Asn Asn
                165                 170                 175

Asn Ile Val Tyr Gly Cys Asn Val Tyr Met Asp Lys Phe Phe Glu Val
            180                 185                 190

Glu Asn Lys Asp Gly Ser Thr Thr Glu Ile Gly Leu Cys Leu Asp Phe
        195                 200                 205

Phe Asp Ser Tyr Lys Ile Ile Thr Cys Ala Glu Ser Gln Phe His Asn
    210                 215                 220

Tyr Val His Asp Val Asp Pro Met Phe Tyr Lys Met Gly Glu Glu Tyr
225                 230                 235                 240

Asp Tyr Asp Thr Trp Arg Ser Pro Thr His Lys Gln Thr Thr Leu Glu
                245                 250                 255
```

```
Leu Arg Tyr Gln Tyr Asn Asp Ile Tyr Met Leu Arg Glu Val Ile Glu
            260                 265                 270

Gln Phe Tyr Ile Asp Gly Leu Cys Gly Gly Glu Leu Pro Leu Thr Gly
        275                 280                 285

Met Arg Thr Ala Ser Ser Ile Ala Phe Asn Val Leu Lys Lys Met Thr
    290                 295                 300

Phe Gly Glu Glu Lys Thr Glu Glu Gly Tyr Ile Asn Tyr Phe Glu Leu
305                 310                 315                 320

Asp Lys Lys Thr Lys Phe Glu Phe Leu Arg Lys Arg Ile Glu Met Glu
                325                 330                 335

Ser Tyr Thr Gly Gly Tyr Thr His Ala Asn His Lys Ala Val Gly Lys
            340                 345                 350

Thr Ile Asn Lys Ile Gly Cys Ser Leu Asp Ile Asn Ser Ser Tyr Pro
        355                 360                 365

Ser Gln Met Ala Tyr Lys Val Phe Pro Tyr Gly Lys Pro Val Arg Lys
    370                 375                 380

Thr Trp Gly Arg Lys Pro Lys Thr Glu Lys Asn Glu Val Tyr Leu Ile
385                 390                 395                 400

Glu Val Gly Phe Asp Phe Val Glu Pro Lys His Glu Glu Tyr Ala Leu
                405                 410                 415

Asp Ile Phe Lys Ile Gly Ala Val Asn Ser Lys Ala Leu Ser Pro Ile
            420                 425                 430

Thr Gly Ala Val Ser Gly Gln Glu Tyr Phe Cys Thr Asn Ile Lys Asp
        435                 440                 445

Gly Lys Ala Ile Pro Val Tyr Lys Glu Leu Lys Asp Thr Lys Leu Thr
    450                 455                 460

Thr Asn Tyr Asn Val Val Leu Thr Ser Val Glu Tyr Glu Phe Trp Ile
465                 470                 475                 480

Lys His Phe Asn Phe Gly Val Phe Lys Lys Asp Glu Tyr Asp Cys Phe
                485                 490                 495

Glu Val Asp Asn Leu Glu Phe Thr Gly Leu Lys Ile Gly Ser Ile Leu
            500                 505                 510

Tyr Tyr Lys Ala Glu Lys Gly Lys Phe Lys Pro Tyr Val Asp His Phe
        515                 520                 525

Thr Lys Met Lys Val Glu Asn Lys Lys Leu Gly Asn Lys Pro Leu Thr
    530                 535                 540

Asn Gln Ala Lys Leu Ile Leu Asn Gly Ala Tyr Gly Lys Phe Gly Thr
545                 550                 555                 560

Lys Gln Asn Lys Glu Glu Lys Asp Leu Ile Met Asp Lys Asn Gly Leu
                565                 570                 575

Leu Thr Phe Thr Gly Ser Val Thr Glu Tyr Glu Gly Lys Glu Phe Tyr
            580                 585                 590

Arg Pro Tyr Ala Ser Phe Val Thr Ala Tyr Gly Arg Leu Gln Leu Trp
        595                 600                 605

Asn Ala Ile Ile Tyr Ala Val Gly Val Glu Asn Phe Leu Tyr Cys Asp
    610                 615                 620

Thr Asp Ser Ile Tyr Cys Asn Arg Glu Val Asn Ser Leu Ile Glu Asp
625                 630                 635                 640

Met Asn Ala Ile Gly Glu Thr Ile Asp Lys Thr Ile Leu Gly Lys Trp
                645                 650                 655

Asp Val Glu His Val Phe Asp Lys Phe Lys Val Leu Gly Gln Lys Lys
            660                 665                 670
```

```
Tyr Met Tyr His Asp Cys Lys Glu Asp Lys Thr Asp Leu Lys Cys Cys
            675                 680                 685

Gly Leu Pro Ser Asp Ala Arg Lys Ile Ile Ile Gly Gln Gly Phe Asp
        690                 695                 700

Glu Phe Tyr Leu Gly Lys Asn Val Glu Gly Lys Lys Gln Arg Lys Lys
705                 710                 715                 720

Val Ile Gly Gly Cys Leu Leu Leu Asp Thr Leu Phe Thr Ile Lys Lys
                725                 730                 735

Ile Met Phe

<210> SEQ ID NO 16
<211> LENGTH: 17
<212> TYPE: PRT
<213> ORGANISM: Artificial Sequence
<220> FEATURE:
<223> OTHER INFORMATION: Linker/TEV/HisTag

<400> SEQUENCE: 16

Gly Leu Ser Ala Glu Asn Leu Tyr Phe Gln Gly His His His His
1               5                   10                  15

His

<210> SEQ ID NO 17
<211> LENGTH: 293
<212> TYPE: PRT
<213> ORGANISM: Artificial Sequence
<220> FEATURE:
<223> OTHER INFORMATION: E111N+126-131G+H144A+K147N alpha-hemolysin

<400> SEQUENCE: 17

Ala Asp Ser Asp Ile Asn Ile Lys Thr Gly Thr Thr Asp Ile Gly Ser
1               5                   10                  15

Asn Thr Thr Val Lys Thr Gly Asp Leu Val Thr Tyr Asp Lys Glu Asn
                20                  25                  30

Gly Met His Lys Lys Val Phe Tyr Ser Phe Ile Asp Asp Lys Asn His
            35                  40                  45

Asn Lys Lys Leu Leu Val Ile Arg Thr Lys Gly Thr Ile Ala Gly Gln
        50                  55                  60

Tyr Arg Val Tyr Ser Glu Glu Gly Ala Asn Lys Ser Gly Leu Ala Trp
65                  70                  75                  80

Pro Ser Ala Phe Lys Val Gln Leu Gln Leu Pro Asp Asn Glu Val Ala
                85                  90                  95

Gln Ile Ser Asp Tyr Tyr Pro Arg Asn Ser Ile Asp Thr Lys Asn Tyr
            100                 105                 110

Met Ser Thr Leu Thr Tyr Gly Phe Asn Gly Asn Val Thr Gly Gly Gly
        115                 120                 125

Gly Gly Gly Ile Gly Gly Leu Ile Gly Ala Asn Val Ser Ile Gly Ala
    130                 135                 140

Thr Leu Asn Tyr Val Gln Pro Asp Phe Lys Thr Ile Leu Glu Ser Pro
145                 150                 155                 160

Thr Asp Lys Lys Val Gly Trp Lys Val Ile Phe Asn Asn Met Val Asn
                165                 170                 175

Gln Asn Trp Gly Pro Tyr Asp Arg Asp Ser Trp Asn Pro Val Tyr Gly
            180                 185                 190

Asn Gln Leu Phe Met Lys Thr Arg Asn Gly Ser Met Lys Ala Ala Asp
        195                 200                 205

Asn Phe Leu Asp Pro Asn Lys Ala Ser Ser Leu Leu Ser Ser Gly Phe
```

```
Ser Pro Asp Phe Ala Thr Val Ile Thr Met Asp Arg Lys Ala Ser Lys
225                 230                 235                 240

Gln Gln Thr Asn Ile Asp Val Ile Tyr Glu Arg Val Arg Asp Asp Tyr
                245                 250                 255

Gln Leu His Trp Thr Ser Thr Asn Trp Lys Gly Thr Asn Thr Lys Asp
            260                 265                 270

Lys Trp Thr Asp Arg Ser Ser Glu Arg Tyr Lys Ile Asp Trp Glu Lys
        275                 280                 285

Glu Glu Met Thr Asn
    290
```

<210> SEQ ID NO 18
<211> LENGTH: 293
<212> TYPE: PRT
<213> ORGANISM: Artificial Sequence
<220> FEATURE:
<223> OTHER INFORMATION: H35G+E111N+H144A+K147N alpha-hemolysin

<400> SEQUENCE: 18

```
Ala Asp Ser Asp Ile Asn Ile Lys Thr Gly Thr Thr Asp Ile Gly Ser
1               5                   10                  15

Asn Thr Thr Val Lys Thr Gly Asp Leu Val Thr Tyr Asp Lys Glu Asn
                20                  25                  30

Gly Met Gly Lys Lys Val Phe Tyr Ser Phe Ile Asp Lys Asn His
            35                  40                  45

Asn Lys Lys Leu Leu Val Ile Arg Thr Lys Gly Thr Ile Ala Gly Gln
50                  55                  60

Tyr Arg Val Tyr Ser Glu Glu Gly Ala Asn Lys Ser Gly Leu Ala Trp
65                  70                  75                  80

Pro Ser Ala Phe Lys Val Gln Leu Gln Leu Pro Asp Asn Glu Val Ala
                85                  90                  95

Gln Ile Ser Asp Tyr Tyr Pro Arg Asn Ser Ile Asp Thr Lys Asn Tyr
            100                 105                 110

Met Ser Thr Leu Thr Tyr Gly Phe Asn Gly Asn Val Thr Gly Asp Asp
        115                 120                 125

Thr Gly Lys Ile Gly Gly Leu Ile Gly Ala Asn Val Ser Ile Gly Ala
    130                 135                 140

Thr Leu Asn Tyr Val Gln Pro Asp Phe Lys Thr Ile Leu Glu Ser Pro
145                 150                 155                 160

Thr Asp Lys Lys Val Gly Trp Lys Val Ile Phe Asn Asn Met Val Asn
                165                 170                 175

Gln Asn Trp Gly Pro Tyr Asp Arg Asp Ser Trp Asn Pro Val Tyr Gly
            180                 185                 190

Asn Gln Leu Phe Met Lys Thr Arg Asn Gly Ser Met Lys Ala Ala Asp
        195                 200                 205

Asn Phe Leu Asp Pro Asn Lys Ala Ser Ser Leu Leu Ser Ser Gly Phe
    210                 215                 220

Ser Pro Asp Phe Ala Thr Val Ile Thr Met Asp Arg Lys Ala Ser Lys
225                 230                 235                 240

Gln Gln Thr Asn Ile Asp Val Ile Tyr Glu Arg Val Arg Asp Asp Tyr
                245                 250                 255

Gln Leu His Trp Thr Ser Thr Asn Trp Lys Gly Thr Asn Thr Lys Asp
            260                 265                 270

Lys Trp Thr Asp Arg Ser Ser Glu Arg Tyr Lys Ile Asp Trp Glu Lys
```

Glu Glu Met Thr Asn
    290

<210> SEQ ID NO 19
<211> LENGTH: 293
<212> TYPE: PRT
<213> ORGANISM: Artificial Sequence
<220> FEATURE:
<223> OTHER INFORMATION: H35G+E111N+M113A+126-131G+H144A+K147N
      alpha-hemolysin

<400> SEQUENCE: 19

Ala Asp Ser Asp Ile Asn Ile Lys Thr Gly Thr Thr Asp Ile Gly Ser
1               5                   10                  15

Asn Thr Thr Val Lys Thr Gly Asp Leu Val Thr Tyr Asp Lys Glu Asn
                20                  25                  30

Gly Met Gly Lys Lys Val Phe Tyr Ser Phe Ile Asp Asp Lys Asn His
            35                  40                  45

Asn Lys Lys Leu Leu Val Ile Arg Thr Lys Gly Thr Ile Ala Gly Gln
        50                  55                  60

Tyr Arg Val Tyr Ser Glu Glu Gly Ala Asn Lys Ser Gly Leu Ala Trp
65                  70                  75                  80

Pro Ser Ala Phe Lys Val Gln Leu Gln Leu Pro Asp Asn Glu Val Ala
                85                  90                  95

Gln Ile Ser Asp Tyr Tyr Pro Arg Asn Ser Ile Asp Thr Lys Asn Tyr
            100                 105                 110

Ala Ser Thr Leu Thr Tyr Gly Phe Asn Gly Asn Val Thr Gly Gly Gly
        115                 120                 125

Gly Gly Gly Ile Gly Gly Leu Ile Gly Ala Asn Val Ser Ile Gly Ala
    130                 135                 140

Thr Leu Asn Tyr Val Gln Pro Asp Phe Lys Thr Ile Leu Glu Ser Pro
145                 150                 155                 160

Thr Asp Lys Lys Val Gly Trp Lys Val Ile Phe Asn Asn Met Val Asn
                165                 170                 175

Gln Asn Trp Gly Pro Tyr Asp Arg Asp Ser Trp Asn Pro Val Tyr Gly
            180                 185                 190

Asn Gln Leu Phe Met Lys Thr Arg Asn Gly Ser Met Lys Ala Ala Asp
        195                 200                 205

Asn Phe Leu Asp Pro Asn Lys Ala Ser Ser Leu Leu Ser Ser Gly Phe
    210                 215                 220

Ser Pro Asp Phe Ala Thr Val Ile Thr Met Asp Arg Lys Ala Ser Lys
225                 230                 235                 240

Gln Gln Thr Asn Ile Asp Val Ile Tyr Glu Arg Val Arg Asp Asp Tyr
                245                 250                 255

Gln Leu His Trp Thr Ser Thr Asn Trp Lys Gly Thr Asn Thr Lys Asp
            260                 265                 270

Lys Trp Thr Asp Arg Ser Ser Glu Arg Tyr Lys Ile Asp Trp Glu Lys
        275                 280                 285

Glu Glu Met Thr Asn
    290

<210> SEQ ID NO 20
<211> LENGTH: 293
<212> TYPE: PRT
<213> ORGANISM: Artificial Sequence
<220> FEATURE:

<223> OTHER INFORMATION: E111N+M113A+126-131G+K147N alpha-hemolysin

<400> SEQUENCE: 20

Ala Asp Ser Asp Ile Asn Ile Lys Thr Gly Thr Thr Asp Ile Gly Ser
1               5                   10                  15

Asn Thr Thr Val Lys Thr Gly Asp Leu Val Thr Tyr Asp Lys Glu Asn
            20                  25                  30

Gly Met His Lys Lys Val Phe Tyr Ser Phe Ile Asp Asp Lys Asn His
        35                  40

<210> SEQ ID NO 22
<211> LENGTH: 293
<212> TYPE: PRT
<213> ORGANISM: Artificial Sequence
<220> FEATURE:
<223> OTHER INFORMATION: E111S-M113S-T145S-K147S-L135I alpha-hemolysin

<400> SEQUENCE: 22

```
Ala Asp Ser Asp Ile Asn Ile Lys Thr Gly Thr Thr Asp Ile Gly Ser
1               5                   10                  15

Asn Thr Thr Val Lys Thr Gly Asp Leu Val Thr Tyr Asp Lys Glu Asn
            20                  25                  30

Gly Met His Lys Lys Val Phe Tyr Ser Phe Ile Asp Asp Lys Asn His
        35                  40                  45

Asn Lys Lys Leu Leu Val Ile Arg Thr Lys Gly Thr Ile Ala Gly Gln
    50                  55                  60

Tyr Arg Val Tyr Ser Glu Glu Gly Ala Asn Lys Ser Gly Leu Ala Trp
65              70                  75                  80

Pro Ser Ala Phe Lys Val Gln Leu Gln Leu Pro Asp Asn Glu Val Ala
                85                  90                  95

Gln Ile Ser Asp Tyr Tyr Pro Arg Asn Ser Ile Asp Thr Lys Ser Tyr
            100                 105                 110

Ser Ser Thr Leu Thr Tyr Gly Phe Asn Gly Asn Val Thr Gly Asp Asp
        115                 120                 125

Thr Gly Lys Ile Gly Gly Ile Ile Gly Ala Asn Val Ser Ile Gly Ala
    130                 135                 140

Ser Leu Ser Tyr Val Gln Pro Asp Phe Lys Thr Ile Leu Glu Ser Pro
145                 150                 155                 160

Thr Asp Lys Lys Val Gly Trp Lys Val Ile Phe Asn Asn Met Val Asn
                165                 170                 175

Gln Asn Trp Gly Pro Tyr Asp Arg Asp Ser Trp Asn Pro Val Tyr Gly
            180                 185                 190

Asn Gln Leu Phe Met Lys Thr Arg Asn Gly Ser Met Lys Ala Ala Asp
        195                 200                 205

Asn Phe Leu Asp Pro Asn Lys Ala Ser Ser Leu Leu Ser Ser Gly Phe
    210                 215                 220

Ser Pro Asp Phe Ala Thr Val Ile Thr Met Asp Arg Lys Ala Ser Lys
225                 230                 235                 240

Gln Gln Thr Asn Ile Asp Val Ile Tyr Glu Arg Val Arg Asp Asp Tyr
                245                 250                 255

Gln Leu His Trp Thr Ser Thr Asn Trp Lys Gly Thr Asn Thr Lys Asp
            260                 265                 270

Lys Trp Thr Asp Arg Ser Ser Glu Arg Tyr Lys Ile Asp Trp Glu Lys
        275                 280                 285

Glu Glu Met Thr Asn
    290
```